(12) United States Patent
Kenley

(10) Patent No.: US 10,758,593 B2
(45) Date of Patent: Sep. 1, 2020

(54) USE OF GROWTH HORMONE FRAGMENTS

(71) Applicant: Metabolic Pharmaceuticals Pty Ltd, Port Melbourne, Victoria (AU)

(72) Inventor: David Kenley, Caulfield North (AU)

(73) Assignee: METABOLIC PHARMACEUTICALS PTY LTD, Port Melbourne, Victoria (AU)

( * ) Notice: Subject to any disclaimer, the term of this patent is extended or adjusted under 35 U.S.C. 154(b) by 0 days.

(21) Appl. No.: 16/136,167

(22) Filed: Sep. 19, 2018

(65) Prior Publication Data

US 2019/0099472 A1    Apr. 4, 2019

Related U.S. Application Data

(62) Division of application No. 14/363,256, filed as application No. PCT/AU2012/001497 on Dec. 7, 2012, now Pat. No. 10,111,933.

(30) Foreign Application Priority Data

| Dec. 9, 2011 | (AU) | ................................ | 2011905132 |
| Dec. 9, 2011 | (AU) | ................................ | 2011905133 |
| Apr. 10, 2012 | (AU) | ................................ | 2012901398 |
| Apr. 10, 2012 | (AU) | ................................ | 2012901400 |

(51) Int. Cl.
   *A61K 38/27*  (2006.01)
   *A61K 35/28*  (2015.01)

(52) U.S. Cl.
   CPC .............. *A61K 38/27* (2013.01); *A61K 35/28* (2013.01)

(58) Field of Classification Search
   None
   See application file for complete search history.

(56) References Cited

U.S. PATENT DOCUMENTS

| 10,111,933 B2 * | 10/2018 | Kenley | .................. A61K 38/27 |
| 2004/0247596 A1 | 12/2004 | Odgren et al. | |
| 2010/0197590 A1 | 8/2010 | Dow et al. | |

FOREIGN PATENT DOCUMENTS

| EP | 1 681 306 A1 | 7/2006 |
| JP | 2006-2204200 A | 8/2006 |
| JP | 2007-536282 A | 12/2007 |
| JP | 2010-505764 A | 2/2010 |
| WO | WO-99/12969 A1 | 3/1999 |
| WO | WO-03/092725 A1 | 11/2003 |
| WO | WO-2005/014033 A1 | 2/2005 |
| WO | WO-2005/040224 A1 | 5/2005 |
| WO | WO-2005/105132 A1 | 11/2005 |
| WO | WO-2006/014678 A2 | 2/2006 |
| WO | WO 2006/133477 | * 12/2006 |
| WO | WO-2006/133477 A1 | 12/2006 |
| WO | WO-2008/042174 A2 | 4/2008 |

OTHER PUBLICATIONS

Prior et al. (Microcirculation. Apr. 2009 ; 16(3): 203-212 (Year: 2009).*
Jung et al. (Int J Oncol. Jul. 2011;39(1):137-43 (Year: 2011).*
Fleming et al. (Curr Opin Orthop. Oct. 2005; 16(5): 354-362 (Year: 2005).*
Kalyani et al., J Gerontol A Biol Sci Med Sci. Jan. 2012; 67A(1): 74-81 (Year: 2012).*
Schulte et al, Obesity, Mortality and Cardiovascular Disease in the Münster Heart Study (PROCAM), Atherosclerosis, vol. 144, pp. 199-209.
International Preliminary Report on Patentability issued in the International Application No. PCT/AU2012/001497 dated Feb. 19, 2014.
Sang Beom Kim et al: "Additive Effects of Intra-articular Injection of Growth Hormone and Hyaluronic Acid in Rabbit Model of Collagenase-induced Osteoarthritis", Journal of Korean Medical Science, vol. 25, No. 5, Jan. 1, 2010 (Jan. 1, 2010), p. 776, XP055213604 ISSN: 1011-8934, DOI: 10.3346/jkms.2010.25.5.776.
Supplementary European Search Report dated Sep. 25, 2015 in co-pending European application No. 12 85 5593.5, 10 pages.
Lun Xue-Gang et al: "Advance In Association of Osteoporosis and Osteoarthritis", China J. Orthop & Trauma, Dec. 2007, vol. 20, No. 12, pp. 876-878.
Office Action dated Feb. 4, 2016, in corresponding Chinese application No. 201280060658.0 and English translation, 18 pages.
Office Action dated Jul. 29, 2016, received in corresponding Japanese Application No. 2014-545042 (8 pages) and English translation (9 pages).
Klinicheckaja revmatologija (edited by Mazurov V.I.), SPb, OOO "Izdatel'stvo Foliant", 2001 [D5], pp. 338-340, scheme 12.1).

(Continued)

*Primary Examiner* — Sergio Coffa
(74) *Attorney, Agent, or Firm* — Foley & Lardner LLP

(57) ABSTRACT

The invention provides a method for treating a condition in which growth hormone administration is beneficial, for treating osteoarthritis, for increasing chondrocyte, proteoglycan or collagen production or quality or repair or promoting cartilage tissue formation or repair, for promoting or improving muscle, ligament or tendon mass, repair, form or function, or for treating inflammatory, traumatic or genetic diseases of muscle or connective tissue, comprising administering to a subject an effective amount of a peptide comprising a carboxyl-terminal sequence from a growth hormone and not the IGF-1 domain of growth hormone. It also provides a method of treating a condition involving insufficient functional chondrocytes or insufficient functional cartilage tissue, the method comprising administering to a subject in need thereof a peptide comprising a carboxyl-terminal sequence from a growth hormone and not the domain of growth hormone responsible for IGF-1 production.

9 Claims, 8 Drawing Sheets
Specification includes a Sequence Listing.

(56) References Cited

OTHER PUBLICATIONS

Office Action dated Nov. 16, 2016, received in corresponding Russian application No. 2014124030/15(039211) 6 pages and English translation (5 pages).
Van Den Berg, WB, Osteoarthritis year 2010 in review: pathomechanisms, Osteoarthritis Cartilage. Apr. 2011; 19(4): 338-41. doi: 10.1016/j.joca.2011.01.022. Epub Feb. 13, 2011 [D5]; retrieved from the Internet at—http://www.sciencedirect.com/science/article/pii/S1063458411000495.
Nöth et al., "Technology Insight: adult mesenchymal stem cells for osteoarthritis therapy," Nat Clin Pract Rheumatol, vol. 4, No. 7, pp. 371-380 (Jul. 2008).
Dr. King "Treatment Options for Osteoarthritis in the Knee," Palo Alto Medical Foundation, downloaded online from URL: <http://www.pamf.org/sports/king/osteoarthritis.html> (Jun. 2009).
Kim et al., "Additive Effects of Intra-articular Injection of Growth Hormone and Hyaluronic Acid in Rabbit Model of Collagenase-induced Osteoarthritis," J Korean Med Sci., vol. 25, pp. 776-780 (2010).
Finke et al., "How to Prevent Osteoarthritis", Health Encyclopedia, downloaded online from URL: <http://www.healthcommunities.com/osteoarthritis/treatment.shtml> (Dec. 2017).
Swierzewski, "Osteoarthritis Treatment, Prevention," HeathCommunities.com, downloaded online from URL: <http://www.healthcommunities.com/osteoarthritis/treatment.shtml> (Dec. 2017).
Jung et al., "Human umbilical cord blood-derived mesenchymal stem cells improve glucose homeostasis in rats with liver cirrhosis," International Journal of Oncology, vol. 39, pp. 137-143 (2011).
Yoshimura et al., "Association of Knee Osteoarthritis with the Accumulation of Metaboic Risk Factors Such as Overweight, Hypertension, Dyslipidemia, and Impaired Glucose Tolerance in Japanese Men and Women: The ROAD Study," The Journal of Rheumatology, vol. 38, No. 5, pp. 921-930 (2011).

* cited by examiner

*1 wk, explant

*1 wk, explant

C2C12 CELLS SHOW MUSCLE DIFFERENTIATION AFTER 24 HOURS OF AOD TREATMENT

*24 hrs treatment, AOD: 100ug/ml

AOD ENHANCES MYOGENIC DIFFERENTIATION

*$p<0.01$, C2C12 cells

USE OF GROWTH HORMONE FRAGMENTS

CROSS-REFERENCE TO RELATED APPLICATIONS

The present application is a divisional of U.S. patent application Ser. No. 14/363,256, filed Jun. 5, 2014 (now U.S. Pat. No. 10,111,933), which is the U.S. National Stage of International Application PCT/AU2012/001497, filed Dec. 7, 2012, and claims priority to Australian Patent Application Nos. 2012901398, filed Apr. 10, 2012, 2012901400, filed Apr. 10, 2012, 2011905132, filed Dec. 9, 2011, and 2011905133, filed Dec. 9, 2011.

FIELD

The invention relates to the use of peptide fragments of growth hormone to treat conditions treatable by growth hormone without the side effects associated with use of growth hormone.

BACKGROUND

All references, including any patents or patent application, cited in this specification are hereby incorporated by reference to enable full understanding of the invention. Nevertheless, such references are not to be read as constituting an admission that any of these documents forms part of the common general knowledge in the art, in Australia or in any other country. The discussion of the references states what their authors assert, and the applicants reserve the right to challenge the accuracy and pertinency of the cited documents.

Somatotropin or growth hormone (GH) is a potent anabolic hormone produced by the pituitary gland in daily doses of 0.5 to 0.8 mg in children and young adults. Its production decreases rapidly with age.

Human growth hormone (hGH) has a number of metabolic effects, the most prominent of which is its anabolic effect. HGH increases the influx of amino acids into the cell and decreases the efflux. Cell proliferation is accentuated as is overall protein synthesis and new tissue growth. HGH also stimulates insulin-like growth factor-1 (IGF-1) production by the liver and the anabolism seen with hGH is due to the action of IGF-1. Additionally, hGH, due to IGF-1 activity, is known to accelerate nucleic acid translation and transcription, increase nitrogen retention, increase protein synthesis, decrease cortisol receptor activity, increase hydrolysis of fats to fatty acids, increase fat oxidation for fuel thereby decreasing fat stores, increase metabolic rate, cause initial fluid retention, produce insulin resistance often leading to hyperglycemia and increase insulin requirements.

The predominant form of hGH is a globular protein with a molecular weight of 22 kilodaltons, consisting of 191 amino acid residues in a single-chain, folded by 2 disulphide bonds with a small loop at the carboxyl terminus between residues 182 and 189. Crystallographic studies show that hGH contains four anti-parallel α-helices which are arranged in a left-twisted, tightly-packed helical bundle. The concept that there are discrete functional domains within the hGH molecule responsible for specific metabolic actions of the hormone is generally accepted. The amino-terminus has been identified as the functional domain responsible for IGF-1 secretion and therefore the insulin-like actions of hGH (Ng (1990) New Antidiabetic Drugs pp 197-205). The carboxyl-terminus has been identified as a lipolytic domain of hGH (Ng F M et al., (2000) J. Mol. Endocrin. 25, 287-298).

HGH serves as a critical hormone in the regulation of cell and organ growth and in physiological function upon various stages of aging. For example, over-production of hGH results in gigantism in children and acromegaly in adults, whereas under-production leads to dwarfism in children, and chronic renal insufficiency. In adults, hGH deficiency can affect metabolic processing of proteins, carbohydrates, lipids, minerals and connective tissue and can result in muscle, bone or skin atrophy. Other hGH deficiency disorders characterized by growth failure include Prader-Willi syndrome, intrauterine growth retardation and catabolic state for example during chemotherapy treatment and in the treatment of AIDS.

Many scientific studies confirm that growth hormone treatment in adults improves the body composition (increasing the muscle mass and decreasing fat), bone density, muscle strength, cardiovascular parameters (i.e. decrease of LDL cholesterol), and the quality of life.

Advanced acquired immunodeficiency syndrome (AIDS) is often accompanied by muscle wasting ("AIDS wasting") and hGH has been shown to ameliorate this condition. HGH has been given to promote healing of large burns by reducing the amount of protein breakdown during the early post-injury period. HGH has been used as an adjunct to caloric restriction for obesity as hGH promotes lipolysis and reduces proteolysis. Several studies have demonstrated improvements in exercise capacity and cardiac function among hGH-deficient patients receiving hGH replacement. Such patients show increased oxygen uptake and power output during cycle ergometry associated with increased skeletal muscle mass and improved cardiac function.

It is widely accepted that the anabolic effects of hGH are mediated via secretion of IGF-1. Elevated IGF-1 may lead to reduced insulin sensitivity, increased hyperglycemic episodes, fluid retention, diabetes, acromegaly and some cancers. Accordingly, clinical applications of hGH are currently restricted.

It is an aim of an embodiment of the present invention to provide treatments for conditions that can be treated by growth hormone, without elevation of IGF-1.

SUMMARY

A first aspect provides a method for:
(a) treating a condition in which growth hormone administration is beneficial,
(b) treating osteoarthritis,
(c) increasing chondrocyte, proteoglycan or collagen production or quality or repair or promoting cartilage tissue formation or repair,
(d) promoting or improving muscle, ligament or tendon mass, repair, form or function, or
(e) treating inflammatory, traumatic or genetic diseases of muscle or connective tissue, comprising administering to a subject an effective amount of a peptide comprising a carboxyl-terminal sequence from a growth hormone and not the domain of growth hormone responsible for IGF-1 production.

An alternative form of the first aspect provides a composition for treatment of a condition in which growth hormone administration is beneficial, for treating osteoarthritis, for increasing chondrocyte, proteoglycan or collagen production or quality or repair or promoting cartilage tissue formation or repair, for promoting or improving muscle, ligament or tendon mass, repair, form or function, or for treating inflammatory, traumatic or genetic diseases of muscle or connective tissue, the composition comprising a peptide comprising a carboxyl-terminal sequence from a growth hormone and not the domain of growth hormone responsible for IGF-1 production.

A further alternative form of the first aspect provides use of a peptide comprising a carboxyl-terminal sequence from a growth hormone and not the domain of growth hormone responsible for IGF-1 production in the manufacture of a medicament for treating a condition in which growth hormone administration is beneficial, for treating osteoarthritis, for increasing chondrocyte, proteoglycan or collagen production or quality or repair or promoting cartilage tissue formation or repair, for promoting or improving muscle, ligament or tendon mass, repair, form or function or for treating inflammatory, traumatic or genetic diseases of muscle or connective tissue.

In an embodiment of the first aspect the condition is not obesity or a bone disorder.

In an embodiment of the first aspect the peptide is capable of enhancing differentiation into myoblasts.

A second aspect provides a method of treating a condition involving insufficient functional chondrocytes or insufficient functional cartilage tissue, the method comprising administering to a subject in need thereof a peptide comprising a carboxyl-terminal sequence from a growth hormone and not the domain of a growth hormone responsible for IGF-1 production.

An alternative form of the second aspect provides a composition for treating a condition involving insufficient functional chondrocytes or insufficient functional cartilage tissue, the composition comprising an effective amount of a peptide comprising a carboxyl-terminal sequence from a growth hormone, and not the domain of a growth hormone responsible for IGF-1 production.

A further alternative form of the second aspect provides use of a peptide comprising a carboxyl-terminal sequence from a growth hormone and not the domain of a growth hormone responsible for IGF-1 production in the manufacture of a medicament for treating a condition involving insufficient functional chondrocytes or insufficient functional cartilage tissue.

In an embodiment of the second aspect the condition is osteoarthritis.

In an embodiment of the first and second aspects the peptide comprises a carboxyl-terminal sequence from human growth hormone or a carboxyl terminal sequence from a growth hormone of a non-human animal.

In an embodiment of the first and second aspects the peptide is capable of promoting chondrocyte production or regeneration. In an embodiment of the first and second aspects the peptide is capable of promoting cartilage tissue production or regeneration. In an embodiment of the first and second aspects the peptide is capable of enhancing differentiation of mesenchymal cells to chondrocytes or cartilage tissue. The methods provide enhanced chondrocyte production or repair. They also enhance cartilage production or repair.

In an embodiment of the first and second aspects the peptide is capable of promoting proteoglycan production. In an embodiment of the first and second aspects the peptide is capable of promoting collagen production. In an embodiment of the first and second aspects the methods promote production of cartilage, chondrocytes and or proteoglycans in damaged cartilage.

In an embodiment of the first and second aspects, the peptide is administered on or in an agent, implant, medical device, prosthesis or cellular scaffold.

In an embodiment of the first and second aspects the condition is one in which a protein anabolic effect is beneficial, including trauma recovery, for treating burns or for promoting growth, repair, strength, form or function of muscle, tendons and ligaments.

In an embodiment of the first and second aspects, the peptide comprises AOD9604 (SEQ ID NO: 1).

In an embodiment of the first and second aspects the peptide consists essentially of AOD9604 (SEQ ID NO: 1).

In an embodiment of the first and second aspects administration of the peptide or medicament does not elevate IGF-1 in serum and hence the treatment provides therapeutic effect in the absence of side effects associated with elevated IGF-1 in serum.

DESCRIPTION

Figure 1:
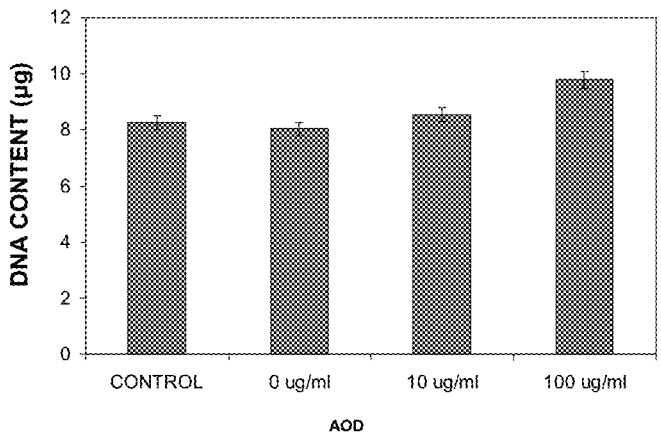
FIG. 1 shows DNA content for chondrocyte culture for 3 weeks on filter with treatment with AOD (SEQ ID NO:1) showing treatment does not have a toxic effect on cells.

Ng, F M et al., (1990) supra identifies the amino-terminus of human growth hormone as the functional domain responsible for IGF-1 secretion and therefore the insulin-like actions of hGH.

In Australian patent No. 693478 by Monash University, the applicant describes the use of a peptide derived from the carboxyl-terminal sequence of human growth hormone, or a corresponding region from growth hormone of other mammalian species, for the control of obesity. This region of growth hormone has the ability to modulate lipid metabolism. In particular, a synthetic peptide corresponding to amino acid residues 177-191 of human growth hormone sequence (hereinafter referred to as hGH 177-191) was found to reduce body weight gain and adipose tissue mass in a model system for obesity, the C57Bl/6J (Ob/Ob) mouse. A subsequent application, PCT/AU98/00724 by Metabolic Pharmaceuticals Ltd, discloses analogues of the hGH177-191 peptide which share this activity. PCT/AU00/01362 (WO01/33977), also by Metabolic Pharmaceuticals Limited, discloses the surprising oral activity of such peptides.

Clinical trials on a particular hGH 177-191 analogue, designated AOD9604 and having the sequence provided as SEQ ID NO: 1 below, showed that the effective dose of the peptide administered did not elevate the plasma level of IGF-1. Hence AOD9604 and other C-terminal growth hormone fragments were shown to have their effect on lipid metabolism distinct from any effect on IGF-1 secretion. This was particularly surprising as it had long been held in the art that the effects of hGH are modulated by IGF-1 secretion. SEQ ID NO: 1 Tyr-Leu-Arg-Ile-Val-Gln-Cys-Arg-Ser-Val-Glu-Gly-Ser-Cys-Gly-Phe (AOD9604 or Tyr-hGH 177-191)

Further work on AOD9604 and other C-terminal growth hormone fragments indicated an effect on bone metabolism, particularly increased osteoblast formation or without an increase in the formation of osteoclasts. This was particularly unexpected as it had been long held in the art that the effect of full length human growth hormone on bone metabolism was through increased IGF-1 secretion, which does not occur with administration of AOD9604. This invention is described in PCT/AU05/00638 to Metabolic Pharmaceuticals Ltd.

The entire disclosures of AUG693478, PCT/AU98/00724, PCT/AU00/01362 and PCT/AU05/00638 are incorporated herein by this reference.

The inventors have now determined that unexpectedly their C-terminal growth hormone fragments, particularly AOD9604 (SEQ ID NO:1) have an anabolic effect on chondrocytes and muscle. Previously it was considered that the anabolic effect of hGH on chondrocytes and muscle was regulated by IGF-1 secretion by human growth hormone and that since the IGF domain was not present in the C-terminal growth hormone fragments that C terminal growth hormone peptides would not have an anabolic effect as they lacked the functional domain of hGH. The inventors have shown this is not the case, thus allowing the treatments with a C terminal growth hormone peptide to proceed without increased IGF-1 secretion and the side effects associated therewith.

For example, the inventors have now determined that C-terminal growth hormone fragments, particularly AOD9604 (SEQ ID NO:1) are capable of increasing chondrocyte, proteoglycan, collagen and production or quality, repair or regeneration and accordingly may improve cartilage production or quality. While previously it was known that human growth hormone stimulates chrondrocyte proliferation it was considered that these treatments resulted in increased IGF-1 secretion. Additionally the inventors have now shown that C-terminal growth hormone fragments can induce differentiation into myoblasts therefore suggesting use of the fragments in conditions requiring muscle growth. The inventors have previously shown that their C-terminal growth hormone fragment does not elevate IGF plasma levels. The new findings provide therapies to proceed without increased IGF-1 secretion and the side effects associated therewith.

Side effects to be avoided include at least one of increased insulin resistance, increased insulin demand, fluid retention, hypercalcaemia and acromegaly.

Treatments

The invention in one aspect relates to the treatment of conditions. The terms "treating" and "treatment" as used herein refer to reduction in severity and/or frequency of symptoms, elimination of symptoms and/or underlying cause, prevention of the occurrence of symptoms (prophylaxis) and/or their underlying cause, and improvement or remediation of damage. Thus, for example, the present method of "treating" a condition encompasses both prevention of the condition in a predisposed individual, treatment of the condition in a clinically symptomatic individual and treatment of a healthy individual for beneficial effect.

"Treating" as used herein covers any treatment of, repair or prevention of a condition in a vertebrate, a mammal, particularly a human or domestic, bloodstock, farm or zoo animal, and includes inhibiting the condition, i.e., arresting its development; or relieving or ameliorating the effects of the condition, i.e., cause regression of the effects of the condition and producing a beneficial effect.

"Prophylaxis" or "prophylactic" or "preventative" therapy as used herein includes preventing the condition from occurring or ameliorating the subsequent progression of the condition in a subject that may be predisposed to the condition, but has not yet been diagnosed as having it.

As used herein, "condition" refers to any deviation from normal health and includes a disease, disorder, defect or injury, such as injury caused by trauma, and deterioration due to age, inflammatory, infectious or genetic disorder or due to environment.

Conditions in which growth factor administration is beneficial are disclosed in the prior art, for example in US2011/0112021 and WO2011/038205. Of those, conditions that may be treated in accordance with the present invention fall generally into the categories of those in which increased chondrocyte, collagen, proteoglycan, cartilage or muscle mass form or function is desirable. Conditions treatable by the present invention include osteoarthritis; rheumatoid arthritis, juvenile rheumatoid arthritis; HIV-infection in children receiving HAART treatment (HIV/HALS children); skeletal dysplasia; hypochondroplasia; achondroplasia; treatment of patients after tendon or ligament surgery in hand, knee, or shoulder; distraction osteogenesis; disorders resulting from hip or discus replacement, meniscus repair, spinal fusions or prosthesis fixation, such as in the knee, hip, shoulder, elbow, wrist or jaw; disorders resulting from fixing of osteosynthesis material, such as nails, screws and plates; non-union or mal-union of fractures; disorders resulting from osteatomia, e.g. from tibia or 1st toe; disorders resulting from graft implantation; articular cartilage degeneration in knee caused by trauma or arthritis; adult patients in chronic dialysis (APCD); malnutritional associated cardiovascular disease in APCD; reversal of cachexia in APCD; chronic abstractive pulmonal disease in APCD; HIV in APCD; elderly with APCD; chronic liver disease in APCD, fatigue syndrome in APCD; impaired liver function; males with HIV infections; HIV-associated lipodystrophy syndrome (HALS); male infertility; treatment of patients after major elective surgery, alcohol/drug detoxification or neurological trauma; aging; frail elderly; traumatically damaged cartilage; fibromyalgia; memory disorders; traumatic brain injury; subarachnoid haemorrhage; very low birth weight;

myocardial fibrosis; idiopathic dilated cardiomyopathy; a neurological disease or disorder; neuro-degeneration; delayed or impaired growth; a cardiovascular disease or disorder; a viral syndrome (such as AIDS); diabetes; complications of diabetes (e.g., retinopathy); anorexia; bulimia; cancer cachexia; AIDS; AIDS wasting; cachexia; wasting; a renal disease or disorder; an inflammatory disease or disorder; inflammation; Prader-Willi syndrome (PWS); chronic renal insufficiency (CRI); aging; end-stage Renal Failure; End stage renal disease (ESRD); Cystic Fibrosis; Erectile dysfunction; HIV lipodystrophy; skeletal dysplasia; Noonan's syndrome; glucocorticoid myopathy; infection; diabetes; hypertension; multiple sclerosis; heart failure; hematoma, ulcerative colitis and burns.

As used therein "neurological disease or disorder" refers to any disease or disorder of the nervous system and or visual system except depression. "Neurological disease or disorder" include disease or disorders that involve the central nervous system (brain, brainstem and cerebellum), the peripheral nervous system (including cranial nerves), and the autonomic nervous system (parts of which are located in both central and peripheral nervous system). Examples of neurological disorders include but are not limited to, headache, stupor and coma, dementia, seizure, sleep disorders, trauma, infections, neoplasms, neuro-opthalmology, movement disorders, demyelinating diseases, spinal cord disorders, and disorders of peripheral nerves, muscle and neuromuscular junctions. The following is a list of several neurological disorders, symptoms, signs and syndromes that may be treated according to the present invention: acquired epileptiform aphasia; acute disseminated encephalomyelitis; adrenoleukodystrophy; age-related macular degeneration; agenesis of the corpus callosum; agnosia; Aicardi syndrome; Alexander disease; Alpers1 disease; alternating hemiplegia; Vascular dementia; amyotrophic lateral sclerosis; anencephaly; Angelman syndrome; angiomatosis; anoxia; aphasia; apraxia; arachnoid cysts; arachnoiditis; AnronI-Chiari malformation; arteriovenous malformation; Asperger syndrome; ataxia telegiectasia; attention deficit hyperactivity disorder, autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; DandyWalker syndrome; Dawson disease; De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahrs syndrome; fainting; familial spastic paralysis; febrile seizures; Fisher syndrome; Friedreich's ataxia; fronto-temporal dementia and other "tauopathies"; Gaucher disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactic a polyncuriuformis; herpes zoster oticus; herpes zoster; Hirayama syndrome; HIV-associated dementia and neuropathy; holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Keams-Sayre syndrome; Kennedy disease Kinsboume syndrome; Klippel Feil syndrome; Krabbe disease; Kugelberg-Welander disease; kuru; Lafora disease; Lambert-Eaton myasthenic syndrome; Landau-Kleflher syndrome; lateral medullary (Wallenberg) syndrome; learning disabilities; Leigh's disease; Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme disease—neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; miltiinfarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae oflupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Neurodegenerative disease or disorder (Parkinson's disease, Huntington's disease, Alzheimer's disease, amyotrophic lateral sclerosis (ALS), dementia, multiple sclerosis and other diseases and disorders associated with neuronal cell death); paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocalleukoencephalopathy; progressive sclerosing poliodystrophy; progressive supranuclear palsy; pseudotumor cerebri; Ramsay-Hunt syndrome (types I and 11); Rasmussen's encephalitis; reflex sympathetic dystrophy syndrome; Refsum disease; repetitive motion disorders; repetitive stress injuries; restless legs syndrome;

retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Wera"nig-Hoffman disease; West syndrome; whiplash; Williams syndrome; Wildon's disease; and Zellweger syndrome.

As used therein an "inflammation" refers to systemic inflammatory conditions and conditions associated locally with migration and attraction of monocytes, leukocytes and/or neutrophils. Examples of inflammation include, but are not limited to, inflammation resulting from infection with pathogenic organisms (including gram-positive bacteria, gram-negative bacteria, viruses, fungi, and parasites such as protozoa and helminths), transplant rejection (including rejection of solid organs such as kidney, liver, heart, lung or cornea, as well as rejection of bone marrow transplants including graft-versus-host disease (GVHD)), or from localized chronic or acute autoimmune disease or allergic reactions.

Autoimmune diseases include acute glomerulonephritis; rheumatoid or reactive arthritis; chronic glomerulonephritis; inflammatory bowel diseases such as Crohn's disease, ulcerative colitis and necrotizing enterocolitis; hepatitis; sepsis; alcoholic liver disease; non-alcoholic steatosis; granulocyte transfusion associated syndromes; inflammatory dermatoses such as contact dermatitis, atopic dermatitis, psoriasis; systemic lupus erythematosus (SLE), autoimmune thyroiditis, multiple sclerosis, and some forms of diabetes, or any other autoimmune state where attack by the subject's own immune system results in pathologic tissue destruction.

Allergic reactions include allergic asthma, chronic bronchitis, acute and delayed hypersensitivity.

Systemic inflammatory disease states include inflammation associated with trauma, burns, reperfusion following ischemic events (e.g. thrombotic events in heart, brain, intestines or peripheral vasculature, including myocardial infarction and stroke), sepsis, ARDS or multiple organ dysfunction syndrome. Inflammatory cell recruitment also occurs in atherosclerotic plaques.

Inflammation includes, but is not limited to, Non-Hodgkin's lymphoma, Wegener's granulomatosis, Hashimoto's thyroiditis, hepatocellular carcinoma, thymus atrophy, chronic pancreatitis, rheumatoid arthritis, reactive lymphoid hyperplasia, osteoarthritis, ulcerative colitis, papillary carcinoma, Crohn's disease, ulcerative colitis, acute cholecystitis, chronic cholecystitis, cirrhosis, chronic sialadenitis, peritonitis, acute pancreatitis, chronic pancreatitis, chronic Gastritis, adenomyosis, endometriosis, acute cervicitis, chronic cervicitis, lymphoid hyperplasia, multiple sclerosis, hypertrophy secondary to idiopathic thrombocytopenic purpura, primary IgA nephropathy, systemic lupus erythematosus, psoriasis, pulmonary emphysema, chronic pyelonephritis, and chronic cystitis. A cardiovascular disease or disorder includes those disorders that can either cause ischemia or are caused by reperfusion of the heart. Examples include, but are not limited to, atherosclerosis, coronary artery disease, granulomatous myocarditis, chronic myocarditis (non-granulomatous), primary hypertrophic cardiomyopathy, peripheral artery disease (PAD), peripheral vascular disease, venous thromboembolism, pulmonary embolism, stroke, angina pectoris, myocardial infarction, cardiovascular tissue damage caused by cardiac arrest, cardiovascular tissue damage caused by cardiac bypass, cardiogenic shock, and related conditions that would be known by those of ordinary skill in the art or which involve dysfunction of or tissue damage to the heart or vasculature, especially, but not limited to, tissue damage related to GH activation.

Cardiovascular diseases include, but are not limited to, atherosclerosis, granulomatous myocarditis, myocardial infarction, myocardial fibrosis secondary to valvular heart disease, myocardial fibrosis without infarction, primary hypertrophic cardiomyopathy, and chronic myocarditis (non-granulomatous).

Other treatments proposed for growth hormone and thus the present invention include nerve repair, pain relief, nerve repair and nerve growth. Prior art also proposes that growth hormone induces keratin growth and thus the present invention can be used to enhance the growth of fingernails and hair and thus be a treatment for baldness and alopecia.

Persons skilled in the art will appreciate that persons affected with one or more of the conditions outlined above could have been treated with hGH in accordance with prior art teaching but that such treatment would have undesirable side effects caused by elevated IGF-1. The inventors accordingly propose that such conditions could be treated with a C-terminal growth hormone fragment as defined herein without elevated IGF-1 and the side effects this causes.

Additionally the inventors have shown particular uses for a C terminal growth hormone fragment that may or may not have been proposed for full length growth hormone.

Chondrocytes are the only cells found in cartilage. They produce and maintain the cartilaginous matrix, which consists mainly of Type II collagen, proteoglycans and elastin.

Cartilage is a flexible connective tissue found in many areas in the bodies of humans and animals, including joints between bones, rib cage, ear, nose, elbow, knee, ankle, bronchial tubes and intervertebral discs. Unlike other connective tissues, cartilage does not contain blood vessels and thus has limited repair capabilities. Because chondrocytes are bound in lacunae, they cannot migrate to damaged areas. Therefore, if cartilage is damaged, it is difficult and slow to heal.

For the purpose of the present disclosure, conditions that can be treated include Chondrocyte-Related Conditions that will benefit from repair or new growth of cartilage tissue or chondrocytes. This is not exclusive however and is used descriptively to emphasise the benefit of the presently disclosed methods.

Chondrocyte-Related Conditions include joint disorders involving cartilage damage and include cartilage damage caused by tibial plateau decompression.

The cause of osteoarthritis is multifactorial and includes body habitus, genetics and hormonal status.

In osteoarthritis, the cartilage covering bones (articular cartilage—a subset of hyaline cartilage) is thinned, eventually completely wearing out, resulting in a "bone against bone" joint, reduced motion and pain. Current therapeutic modalities are aimed at reducing pain and increasing joint function. Non-invasive interventions such as exercise and weight loss are the first lines of treatment, followed by anti-inflammatory medications. These latter treatments alleviate the symptoms but do not inhibit the processes that result in the changes characteristic of this disease and may actually accelerate joint destruction. Failure of these treatments usually culminates in surgical intervention (arthroplasty). Joint replacement is extremely successful with respect to restoring patient mobility and decreasing pain. However, failure as a result of osteolysis and aseptic loosening due to effects of wear debris or biomechanically-related bone loss limit the lifetime of these implants necessitating higher-risk revision surgery at the expense of increased patient morbidity and failure rate. The present invention provides a treatment for osteoarthritis.

In traumatic rupture or detachment, the cartilage in the knee is frequently damaged, and can be partially repaired through knee cartilage replacement therapy.

In achondroplasia, reduced proliferation of chondrocytes in the epiphyseal plate of long bones during infancy and childhood results in dwarfism.

Costochondritis is an inflammation of cartilage in the ribs, causing chest pain.

In spinal disc herniation, an asymmetrical compression of an intervertebral disc ruptures the sac-like disc, causing a herniation of its soft content. The hernia often compresses the adjacent nerves and causes back pain.

In relapsing polychondritis, a destruction, probably auto-immune, of cartilage, especially of the nose and ears, causes disfiguration. Death occurs by suffocation as the larynx loses its rigidity and collapses.

Tumours made up of cartilage tissue, either benign or malignant, can occur.

The present invention provides a treatment for each of the conditions above. Any of these conditions can be treated by repairing or growing new cartilage or chondrocytes according to the methods disclosed herein utilising a peptide comprising a C-terminus of a GH, or composition thereof.

Other conditions that may be treated in accordance with the invention include: chondromalacia patella; chondromalacia; chondrosarcoma-head and neck; chondrosarcoma; costochondritis; enchondroma; hallux rigidus; hip labral tear; osteochondritis dissecans (OCD); osteochondrodysplasias; perichondritis; polychondritis; or torn meniscus.

The invention provides means to improve the function of existing chondrocytes and cartilage in maintaining a cartilaginous matrix. It also provides means to promote growth of chondrocytes and cartilage and provide a cartilaginous matrix, with or without an implant or prosthesis. In one embodiment the invention provides means to promote cartilage formation or repair in a cellular scaffold or in tissue engineering techniques, for example for cartilage generation or repair to grow new cartilage tissue in tissues including the nose, septum, ear, elbow, knee, ankle and invertebrate discs.

In one aspect the peptide is administered with an implant or the like to produce or repair chondrocytes or cartilage tissue that may interact with the implant to treat a condition as disclosed herein. As used herein, "interact" refers to the effect in conjunction of components to achieve a desired biological outcome.

While not wishing to be bound by theory, when an implant "interacts" with chondrocytes, the effect of the implant in treating the condition is greater than the effect of the implant alone and may be synergistic.

In one aspect the peptide is administered in combination with mesenchymal stem cells therapies to enhance repair. The effect of treatment with the peptide and stem cells may be more than the additive effect of the separate treatments and may be synergistic.

In this embodiment, the "desired biological outcome" provided by the invention is preferably cartilage repair and cartilage growth, more preferably removal of the symptoms of osteoarthritis and most preferably treatment and prevention of osteoarthritis.

In another example, the inventors show that a C-terminal growth hormone fragment, particularly AOD9604 (SEQ ID NO:1) can be used to promote muscle growth, to improve recovery of muscle from injury, trauma or use, to improve muscle strength, to improve exercise tolerance, to increase the proportion of muscle, to increase muscle mass, decrease muscle wasting, improve muscle repair, or may be useful to treat disorders of muscle including wasting disorders, such as cachexia, and hormonal deficiency, anorexia, AIDS wasting syndrome, sarcopenia, muscular dystrophies, neuromuscular diseases, motor neuron diseases, diseases of the neuromuscular junction, and inflammatory myopathies in a subject in need thereof.

The invention extends to treatment of disorders of muscle and of diseases associated with muscular degeneration characteristics. Non limiting examples of such disorders are various neuromuscular diseases, cardiac insufficiency, weakness of single muscles such as e.g. the constrictor or bladder muscle, hypo- or hypertension caused by problems with the constrictor function of vascular smooth muscle cells, impotence/erectile dysfunction, incontinence, AIDS-related muscular weakness, and general and age-related amyotrophia.

Disorders of muscle as referred to herein particularly include muscle wasting conditions or disorders in which muscle wasting is one of the primary symptoms.

"Muscle wasting" refers to the progressive loss of muscle mass and/or to the progressive weakening and degeneration of muscles, including the skeletal or voluntary muscles which control movement, cardiac muscles which control the heart, and smooth muscles. In one embodiment, the muscle wasting condition or disorder is a chronic muscle wasting condition or disorder. "Chronic muscle wasting" is defined herein as the chronic (i.e. persisting over a long period of time) progressive loss of muscle mass and/or to the chronic progressive weakening and degeneration of muscle. Chronic muscle wasting may occur as part of the aging process.

The loss of muscle mass that occurs during muscle wasting can be characterized by a muscle protein breakdown or degradation, by muscle protein catabolism. Protein catabolism occurs because of an unusually high rate of protein degradation, an unusually low rate of protein synthesis, or a combination of both. Protein catabolism or depletion, whether caused by a high degree of protein degradation or a low degree of protein synthesis, leads to a decrease in muscle mass and to muscle wasting. The term "catabolism" has its commonly known meaning in the art, specifically an energy burning form of metabolism.

Muscle wasting can occur as a result of age, a pathology, disease, condition or disorder. In one embodiment, the pathology, illness, disease or condition is chronic. In another embodiment, the pathology, illness, disease or condition is genetic. In another embodiment, the pathology, illness, disease or condition is neurological. In another embodiment, the pathology, illness, disease or condition is infectious. As described herein, the pathologies, diseases, conditions or disorders directly or indirectly produce a wasting (i.e. loss) of muscle mass, that is a muscle wasting disorder.

Also contemplated is the treatment of neuromuscular diseases which are aligned with joint or skeletal deformities. In one embodiment, muscle wasting in a subject is a result of the subject having a muscular dystrophy; muscle atrophy; or X-linked spinal-bulbar muscular atrophy (SBMA).

The muscular dystrophies are genetic diseases characterized by progressive weakness and degeneration of the skeletal or voluntary muscles that control movement. The muscles of the heart and some other involuntary muscles are also affected in some forms of muscular dystrophy. The major forms of muscular dystrophy (MD) are: Duchenne muscular dystrophy, myotonic dystrophy, Becker muscular dystrophy, limb-girdle muscular dystrophy, facioscapulohumeral muscular dystrophy, congenital muscular dystrophy, oculopharyngeal muscular dystrophy, distal muscular dystrophy and Emery-Dreifuss muscular dystrophy.

Muscular dystrophy can affect people of all ages. Although some forms first become apparent in infancy or childhood, others may not appear until middle age or later. Duchenne MD is the most common form, typically affecting children. Myotonic dystrophy is the most common of these diseases in adults.

Muscle atrophy (MA) is characterized by wasting away or diminution of muscle and a decrease in muscle mass. For example, Post-Polio MA is a muscle wasting that occurs as part of the post-polio syndrome (PPS). The atrophy includes weakness, muscle fatigue, and pain.

Another type of MA is X-linked spinal-bulbar muscular atrophy (SBMA—also known as Kennedy's Disease). This disease arises from a defect in the androgen receptor gene on the X chromosome, affects only males, and its onset is in adulthood.

Sarcopenia is a debilitating disease that afflicts the elderly and chronically ill patients and is characterized by loss of muscle mass and function. Further, increased lean body mass is associated with decreased morbidity and mortality for certain muscle-wasting disorders. In addition, other circumstances and conditions are linked to, and can cause muscle wasting disorders. For example, studies have shown that in severe cases of chronic lower back pain, there is paraspinal muscle wasting.

Muscle wasting and other tissue wasting is also associated with advanced age. It is believed that general weakness in old age is due to muscle wasting. As the body ages, an increasing proportion of skeletal muscle is replaced by fibrous tissue. The result is a significant reduction in muscle power, performance and endurance.

Long term hospitalization due to illness or injury, or disuse deconditioning that occurs, for example, when a limb is immobilized, can also lead to muscle wasting, or wasting of other tissue. Studies have shown that in patients suffering injuries, chronic illnesses, burns, trauma or cancer, who are hospitalized for long periods of time, there is a long-lasting unilateral muscle wasting, and a decrease in body mass.

Injuries or damage to the central nervous system (CNS) are also associated with muscle wasting and other wasting disorders. Injuries or damage to the CNS can be, for example, caused by diseases, trauma or chemicals. Examples are central nerve injury or damage, peripheral nerve injury or damage and spinal cord injury or damage. In one embodiment CNS damage or injury comprise Alzheimer's diseases (AD); stroke, anger (mood); anorexia, anorexia nervosa, anorexia associated with aging and/or assertiveness (mood).

In another embodiment, muscle wasting or other tissue wasting (e.g. tendons or ligaments) may be a result of alcoholism.

In one embodiment, the wasting disease, disorder or condition being treated is associated with chronic illness This embodiment is directed to treating, in some embodiments, any wasting disorder, which may be reflected in muscle wasting, weight loss, malnutrition, starvation, or any wasting or loss of functioning due to a loss of tissue mass.

In some embodiments, wasting diseases or disorders, such as cachexia, including cachexia caused by malnutrition, tuberculosis, leprosy, diabetes, renal disease, chronic obstructive pulmonary disease (COPD), cancer, end stage renal failure, emphysema, osteomalacia, or cardiomyopathy, may be treated by the methods of this invention In some embodiments, wasting is due to infection with enterovirus, Epstein-Barr virus, herpes zoster, HIV, trypanosomes, influenza, coxsackie, rickettsia, trichinella, schistosoma or mycobacteria.

Cachexia is weakness and a loss of weight caused by a disease or as a side effect of illness. Cardiac cachexia, i.e. a muscle protein wasting of both the cardiac and skeletal muscle, is a characteristic of congestive heart failure. Cancer cachexia is a syndrome that occurs in patients with solid tumours and haematological malignancies and is manifested by weight loss with massive depletion of both adipose tissue and lean muscle mass.

Cachexia is also seen in COPD, acquired immunodeficiency syndrome (AIDS), human immunodeficiency virus (HIV)-associated myopathy and/or muscle weakness/wasting is a relatively common clinical manifestation of AIDS. Individuals with HIV-associated myopathy or muscle weakness or wasting typically experience significant weight loss, generalized or proximal muscle weakness, tenderness, and muscle atrophy.

Untreated muscle wasting disorders can have serious health consequences. The changes that occur during muscle wasting can lead to a weakened physical state resulting in poor performance of the body and detrimental health effects.

Thus, muscle atrophy can seriously limit the rehabilitation of patients after immobilizations. Muscle wasting due to chronic diseases can lead to premature loss of mobility and increase the risk of disease-related morbidity. Muscle wasting due to disuse is an especially serious problem in elderly, who may already suffer from age-related deficits in muscle function and mass, leading to permanent disability and premature death as well as increased bone fracture rate. Despite the clinical importance of the condition few treatments exist to prevent or reverse the condition. The inventors propose that the peptide can be used to prevent, repair and treat muscle wasting or atrophy associated with any of the conditions recited above.

In a preferred embodiment the peptide is used to treat burns and sepsis. Human GH has been shown to have beneficial anabolic effects in treating patients after major surgery, trauma, sepsis, and burns.

Ramirez (1998) Ann Surg; 228, No. 4: 439-448 reports a study of the safety and efficacy of hGH in the treatment of children who are severely burned. The effect of hGH was manifested through elevated IGF-1 and this caused decreased glucose uptake, inhibition of glucose oxidation and a deficiency in glucose transport leading to elevated serum glucose. While this can be treated with insulin this is not a desirable outcome. The inventors propose that the methods of the present invention allow treatment of burns without the associated side effects of elevated IGF-1 as the C-terminal growth hormone fragment has the muscle anabolic effects of human GH without containing an IGF-1 domain and thus without having a measurable effect on IGF-1.

The invention in other aspects also contemplates treating healthy individuals to cause an increase in muscle mass, strength, function or overall physique. Full length growth hormone has been proposed to promote muscle recovery from injury or trauma or damage or overuse through training and therefore to increase exercise tolerance. The inventors propose that C-terminal growth hormone fragments may have the same effect but without the side effects of elevated IGF-1.

The term "increase in muscle mass" refers to the presence of a greater amount of muscle after treatment relative to the amount of muscle mass present before the treatment.

The term "increase in muscle strength" refers to the presence of a muscle with greater force generating capacity after treatment relative to that present before the treatment.

The term "increase in muscle function" refers to the presence of muscle with greater variety of function after treatment relative to that present before the treatment.

The term "increase in exercise tolerance" refers to the ability to exercise with less rest between exercise after treatment relative to that needed before the treatment.

A muscle is a tissue of the body that primarily functions as a source of power. There are three types of muscles in the body: a) skeletal muscle—striated muscle responsible for generating force that is transferred to the skeleton to enable movement, maintenance of posture and breathing; b) cardiac muscle—the heart muscle; and c) smooth muscle—the muscle that is in the walls of arteries and bowel. The methods of the invention are particularly applicable to skeletal muscle but may have some effect on cardiac and or smooth muscle. Reference to skeletal muscle as used herein also includes interactions between bone, muscle and tendons and includes muscle fibres and joints.

Peptides

The invention utilises a peptide comprising a carboxyl-terminal growth hormone fragment.

The terms carboxyl-terminal and C-terminal can be used interchangeably.

In one embodiment the invention utilises a peptide comprising a carboxyl-terminal fragment of human growth hormone. In one embodiment the invention utilises a peptide comprising a carboxyl-terminal fragment of a non-human growth hormone.

The published corresponding sequences of the C-terminal region of the growth hormone of selected mammals are tabulated below, using standard single letter notation. It will be apparent to persons skilled in the art that amino acid sequences of other animal growth hormones are available and they can also be used to design a peptide for use in accordance with the invention.

| GH Species | Sequence | SEQ ID |
|---|---|---|
| human | FRKDMDKVETFLR I VQCR SVEGSCGF | 2 |
| human variant | FRKDMDKVETFLR I VQCR SVEGSCGF | 3 |
| human CS | FRKDMDKVETFLRMVQCR SVEGSCGF | 4 |
| monkey, rhesus | FRKDMDK I ETFLR I VQCR SVEGSCGF | 5 |
| rat | FKKDLHKAETYLRVMKCRRFAESSCAF | 6 |
| mouse | FKKDLHKAETYLRVMKCRRFAESSCAF | 7 |
| hamster | FKKDLHKAETYLRVMKCRRFAESSCAF | 8 |
| whale, fin | FKKDLHKAETYLRVMKCRRFVESSCAF | 9 |
| whale, sei | FKKDLHKAETYLRVMKCRRFVESSCAF | 10 |
| fox, dog, cat | FKKDLHKAETYLRVMKCRRFVESSCAF | 11 |
| mink | FKKDLHKAETYLRVMKCRRFVESSCAF | 12 |
| cattle | FRKDLHKTETYLRVMKCRRFGEASCAF | 13 |
| sheep | FRKDLHKTETYLRVMKCRRFGEASCAF | 14 |
| goat | FRKDLHKTETYLRVMKCRRFGEASCAF | 15 |
| pig | FKKDLHKAETYLRVMKCRRFVESSCAF | 16 |
| alpaca | FKKDLHKAETYLRVMKCRRFVESSCAF | 17 |
| horse | FKKDLHKAETYLRVMKCRRFVESSCAF | 18 |
| elephant | FKKDLHKAETYLRVMKCRRFVESSCAF | 19 |
| ancestral mammal | FKKDLHKAETYLRVMKCRRFVESSCAF | 20 |

The present invention also extends to the use of peptides which are functional homologues or variants of the native carboxyl-terminal sequences of human growth hormone or growth hormone of other animal species.

These functional homologues or variants may be derived by insertion, deletion or substitution of amino acids in, or chemical modification of, the native carboxyl-terminal sequence. Amino acid insertion variants include amino and/or carboxylic terminal fusions as well as intra-sequence insertions of single or multiple amino acids. Insertion amino acid sequence variants are those in which one or more amino acid residues are introduced into a predetermined site in the protein although random insertion is also possible with suitable screening of the resulting product. Deletion variants are characterised by the removal of one or more amino acids from the sequence. Substitution amino acid variants are those in which at least one amino acid residue in the sequence has been replaced by another of the twenty primary protein amino acids, or by a non-protein amino acid. In one embodiment substitutions are with conservative amino acids. Chemical modifications of the native carboxyl-terminal sequence include the acetylation of the amino-terminus and/or amidation of the carboxyl-terminus and/or side chain cyclisation of the native carboxyl-terminal sequence.

In one embodiment variants may comprise one, two, three, four or five insertions, deletions or substitutions compared to the natural growth hormone C-terminal sequence provided that the function of the native C-terminal sequence is retained.

In one embodiment variants include a disulphide bond which confers a cyclic configuration on the peptide. In particular, use of all of the active peptides disclosed in AU 693478 and PCT/AU98/00724 is to be understood to be within the scope of this invention, for example:

wherein the amino acid residue abbreviations used are in accordance with the standard peptide nomenclature:
Gly=Glycine; Ile=Isoleucine; Glu=Glutamic Acid; Phe=Phenylalanine;
Cys=Cysteine; Arg=Arginine; Gln=Glutamine; Leu=Leucine; Ser=Serine; Val=Valine;
Lys=Lysine; Ala=Alanine; Asp=Aspartic acid; His=Histidine; Orn=Ornithine;
Tyr=Tyrosine; Pen=Penicillamine(p, p'-Dimethyl-Cysteine).

In one embodiment amino acids, except for glycine, are of the L-absolute configuration. D configuration amino acids may also be used. The peptide may have a cyclic disulfide bond between Cys(182) and Cys(189) or Pen(182) and Pen(189) as appropriate.

Persons skilled in the art will appreciate that the peptide used may be modified to improve storage stability, bioactivity, circulating half life, or for any other purpose using methods available in the art, such as glycosylation, by conjugation to a polymer to increase circulating half-life, by pegylation or other chemical modification.

For example it may be desirable to introduce modification to improve storage stability or to improve bioavailability.

In one embodiment the peptide comprises amino acids 182-189 (hGH 182-189), amino acids 181-189, 180-189, 179-189, 178-189, 177-189, 176-189, 175-189, 175-190, 176-190, 177-190, 178-190, 179-190, 180-190, 181-190,

| Ref No. | STRUCTURE | |
|---|---|---|
| 9502 | Leu Arg Ile Val Gln Pen Arg Ser Val Glu Gly Ser Pen Gly Phe | SEQ ID NO: 21 |
| 9405 | CH3CO-Leu Arg Ile Val Gln Cys Arg Ser Val Glu Gly Ser Cys Gly Phe | SEQ ID NO: 22 |
| 9410 | H-Leu Arg Ile Val Gln Cys Arg Ser Val Glu Gly Ser Cys Gly Phe | SEQ ID NO: 23 |
| 9404 | Leu Arg Ile Val Gln Cys Arg Ser Val Glu Gly Ser Cys Gly Phe-CONH$_2$ | SEQ ID NO: 24 |
| 9407 | Leu Arg Ile Val Gln Cys Lys Ser Val Glu Gly Ser Cys Gly Phe | SEQ ID NO: 25 |
| 9408 | Leu Arg Ile Val Gln Cys <u>Lys Ser Val Glu</u> Gly Ser Cys Gly Phe<br>(amide bond) | SEQ ID NO: 26 |
| 9604 | Tyr Leu Arg Ile Val Gln Cys Arg Ser Val Glu Gly Ser Cys Gly Phe | SEQ ID NO: 1 |
| 9605 | Lys Leu Arg Ile Val Gln Cys Arg Ser Val Glu Gly Ser Cys Gly Phe | SEQ ID NO: 27 |
| 9618 | Lys Lys Leu Arg Ile Val Gln Cys Arg Ser Val Gln Gly Ser Cys Gly Phe | SEQ ID NO: 28 |
| 9607 | Ala Arg Ile Val Gln Cys Arg Ser Val Glu Gly Ser Cys Gly Phe | SEQ ID NO: 29 |
| 9606 | Leu Lys Ile Val Gln Cys Arg Ser Val Glu Gly Ser Cys Gly Phe | SEQ ID NO: 30 |
| 9608 | Leu Arg Ala Val Gln Cys Arg Ser Val Glu Gly Ser Cys Gly Phe | SEQ ID NO: 31 |
| 9403 | Leu Arg Lys Val Gln Cys Arg Ser Val Glu Gly Ser Cys Gly Phe | SEQ ID NO: 32 |
| 9609 | Leu Arg Ile Ala Gln Cys Arg Ser Val Glu Gly Ser Cys Gly Phe | SEQ ID NO: 33 |
| 9610 | Leu Arg Ile Val Ala Cys Arg Ser Val Glu Gly Ser Cys Gly Phe | SEQ ID NO: 34 |
| 9612 | Leu Arg Ile Val Gln Cys Arg Ala Val Glu Gly Ser Cys Gly Phe | SEQ ID NO: 35 |
| 9613 | Leu Arg Ile Val Gln Cys Arg Ser Ala Glu Gly Ser Cys Gly Phe | SEQ ID NO: 36 |
| 9615 | Leu Arg Ile Val Gln Cys Arg Ser Val Glu Ala Ser Cys Gly Phe | SEQ ID NO: 37 |
| 9616 | Leu Arg Ile Val Gln Cys Arg Ser Val Glu Gly Ala Cys Gly Phe | SEQ ID NO: 38 |
| 9602 | Leu Arg Ile Val Gln Cys Arg Ser Val Glu Gly Ser Cys Ala Phe | SEQ ID NO: 39 |
| 9501 | Leu Arg Ile Val Gln Cys Arg Ser Val Glu D-Ala Ser Cys D-Ala Phe | SEQ ID NO: 40 |
| 9601 | Leu Arg Ile Val Gln Cys Arg Ser Val Glu Gly Ser Cys Gly Ala | SEQ ID NO: 41 |

182-190, 182-191, 181-191, 180-191, 179-191, 178-191, 177-191, 176-191 or 175-191 of human growth hormone or corresponding peptides from growth hormone of non-human animals, for example from within SEQ ID NO: 2-20.

In one embodiment the peptide comprises a variant of a C-terminal fragment of hGH comprising amino acids 182-189 or particularly 177-191. In a preferred embodiment the peptide is AOD9604 (Tyr-hGH 177-191) SEQ ID NO: 1.

"Peptide" as used herein means any chain of amino acids from 8 to 50 amino acid residues in length, preferably 8 to 40, 8 to 30, 8 to 25, or 8 to 20, or more preferably about 8, 9, 10, 11, 12, 13, 14, 15, 16, 17, 18 or 19 amino acid residues in length.

Any peptide for use in accordance with the present invention cannot have the full length sequence of a growth hormone. Full length growth hormone is effective for the treatments proposed but also increases secretion of IGF-1. Accordingly full length growth hormone does not fall within the scope of the peptides for use in accordance with the present invention.

Any peptide for use in accordance with the present invention cannot have the full length sequence of a growth hormone as the peptide for use in the present invention cannot contain the domain of growth hormone responsible for IGF-1 production. As used herein the domain of growth hormone responsible for IGF-1 production is amino acid residues 6-14 of human growth hormone.

A peptide for use in accordance with the present invention may be derived from natural sources, produced by recombinant DNA technology, or synthesised using conventional peptide synthetic methods.

The peptide may be conjugated to a fusion partner to enable easier biosynthesis and/or delivery. It may be incorporated in a conventional pharmaceutical composition, or may be present in a genetically-modified food, such as disclosed in WO 01/33997.

Administration

The peptide may be administered in a pharmaceutical composition together with a pharmaceutically acceptable carrier for administration.

The peptide may be administered by any suitable route, and the person skilled in the art will readily be able to determine the most suitable route and dose for the condition to be treated and the subject. The peptide may be administered orally, sublingually, buccally, intranasally, by inhalation, transdermally, topically, intra-articularly or parenterally in dosage unit formulations containing conventional non-toxic pharmaceutically acceptable carriers, adjuvants, and vehicles. The term parenteral as used herein includes subcutaneous, intravenous, intramuscular, intrathecal, intracranial, injection or infusion techniques.

In one embodiment the peptide may be administered with or in an implant, medical device or prosthesis. The implant may be a biodegradable implant or slow release depot or other implant as known to persons skilled in the art. Such embodiment is particularly appropriate for improving muscle growth and strength after muscle trauma or damage.

When used to treat burns the peptide may be administered orally, topically or parenterally.

Compositions comprising the peptide are to be administered in a therapeutically effective amount. As used herein, an "effective amount" is a dosage which is sufficient to reduce to achieve a desired biological outcome. The desired biological outcome may be any therapeutic benefit including an increase in muscle mass, an increase in muscle strength, muscle growth, or treatment of burns or wounds. Such improvements may be measured by a variety of methods including those that measure lean and fat body mass (such as duel ray scanning analysis), muscle strength, or the formation of muscle cells.

A typical daily dosage might range from about 1 μg/kg to up to 100 mg/kg or more, depending on the mode of delivery.

Dosage levels of the growth hormone fragment could be of the order of about 0.1 mg per day to about 50 mg per day, or will usually be between about 0.25 mg to about 1 mg per day. The amount of active ingredient which may be combined with the carrier materials to produce a single dosage will vary, depending upon the host to be treated and the particular mode of administration. For example, a formulation intended for oral administration to humans may contain about 1 mg to 1 g of an active compound with an appropriate and convenient amount of carrier material, which may vary from about 5 to 95 percent of the total composition. Dosage unit forms will generally contain between from about 0.1 mg to 50 mg of active ingredient.

It will be understood, however, that the specific dose level for any particular subject will depend upon a variety of factors including the activity of the specific compound employed, the age, body weight, general health, sex, diet, time of administration, route of administration, rate of excretion, drug combination and the severity of the particular disease undergoing therapy.

Dosage schedules can be adjusted depending on the half life of the peptide, or the severity of the subject's condition.

Generally, the compositions are administered as a bolus dose, to maximize the circulating levels of peptide for the greatest length of time after the dose. Continuous infusion may also be used after the bolus dose.

Subject

The treatments of the present invention are suitable for subjects in need thereof. "Subject," as used herein, refers to human and non-human animals.

The term "non-human animals" includes all vertebrates, e.g., mammals, such as non-human primates (particularly higher primates), sheep, horse, dog, rodent (e.g., mouse or rat), guinea pig, goat, pig, cat, rabbits, cow, and non-mammals, such as chickens, amphibians, reptiles, etc. In one embodiment, the subject is an experimental animal, an animal suitable as a disease model, or in animal husbandry (animals as food source), where methods to increase lean muscle mass will greatly benefit the industry. Additionally the method of the first aspect is particularly important in race horses.

In one embodiment the treatment is for humans, particularly adult humans, children aged 11 to 16 years old, aged 4 to 10 years old, infants of 18 months up to 4 years old, babies up to 18 months old. The treatment may also be used for elderly or infirm humans.

In one embodiment the subject is suffering from a disease, for example osteoarthritis, diabetes, HIV, or is immunocompromised. The subject may possess pre-diabetic markers or have a disease in which diabetes in a complication. In another embodiment the subject is desirous of an improvement in their health or appearance, for example to slow aging or improve physique. Subjects therefore include athletes, both elite and amateur, body builders, those desirous of enhanced physique, combatants and manual workers.

In one embodiment the treatments of the present invention are used to supplement alternative treatments for the same condition. For example the C-terminal growth hormone fragment can be used to supplement stem cell therapies for joint and muscle repair.

In one embodiment the subject is contraindicated for growth hormone therapy.

Throughout this specification and claims which follow, unless the context requires otherwise, the word "comprise", or variations such as "comprises" or "comprising", will be understood to imply the inclusion of a stated integer or group of integers but not the exclusion of any other integer or group of integers.

It must also be noted that, as used in the subject specification, the singular forms "a", "an" and "the" include plural aspects unless the context clearly dictates otherwise.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

The invention will now be described by way of reference only to the following non-limiting examples.

EXAMPLES

Example 1: Determine the Effect of AOD on Cartilage Repair by Evaluating Tissue Formation Methods
Cell Culture and Treatment Chondrocytes were isolated from articular cartilage obtained aseptically from calf metacarpal-carpal joints and seeded onto collagen type II-coated membrane inserts (Millipore™) ($1.5 \times 10^6$ cells/12 mm diameter membrane). Chondrocytes were grown in Ham's F-12 supplemented with 5% fetal bovine serum (FBS) under standard culture conditions. After 5 days the serum was increased to 20%. Chondrocytes were then grown in the presence and absence of AOD9604 (SEQ ID NO: 1) (10 or 100 µg/ml) for 2 weeks (total culture time 3 weeks). Fresh AOD was added with each change of media.

Assessment of Tissue

The tissue was harvested and digested with papain (Sigma, 40 µg/ml) for 48 h at 65° C. DNA content was determined using the Hoechst 33258 dye binding assay (Polysciences) and fluorometry (excitation 365 nm, emission 458 nm). Proteoglycan content was determined by measuring the amount of sulphated glycosaminoglycans using the dimethylmethylene blue dye binding assay and spectrophotometry (525 nm). Collagen content was determined by measuring the hydroxyproline content of an aliquot of the papain digest hydrolyzed in 6N HCl for 18 h at 110° C. The hydroxyproline content was determined using the chloramine-T/Ehrlich's reagent assay and spectrophotometry (560 nm). The cellularity was quantified by measuring the DNA content using Hoescht 33258 dye binding assay (Polysciences) and fluorometry (excitation 365 nm, emission 458 nm).

Statistical Analysis

All experiments were done three times and each condition was done in triplicate. The data was expressed as mean±SD. The data was expressed as mean±SD. Significance was determined using two way ANOVA followed by Tukey's post hoc test when multiple groups were being evaluated. T test was utilized if 2 groups were being compared. Significance was assigned at p values <0.05.

Results

AOD9604 treatment was not toxic to the cells as determined by quantifying DNA content after 2 weeks of treatment (FIG. 1).

Figure 2:
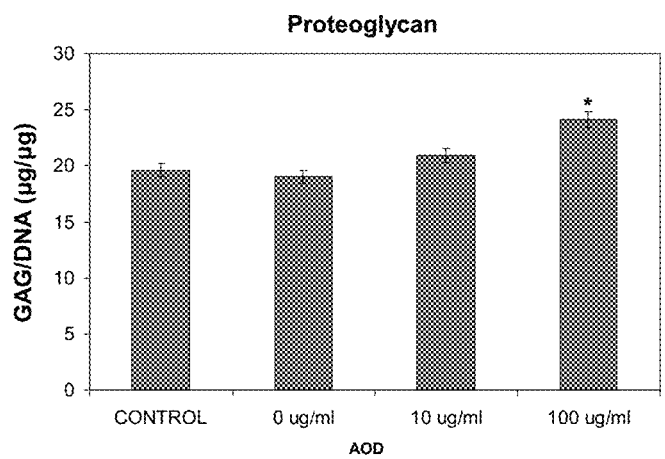
FIG. 2 shows proteoglycan content for chondrocyte culture for 3 weeks on filter with treatment with AOD (SEQ ID NO:1).
Figure 3:
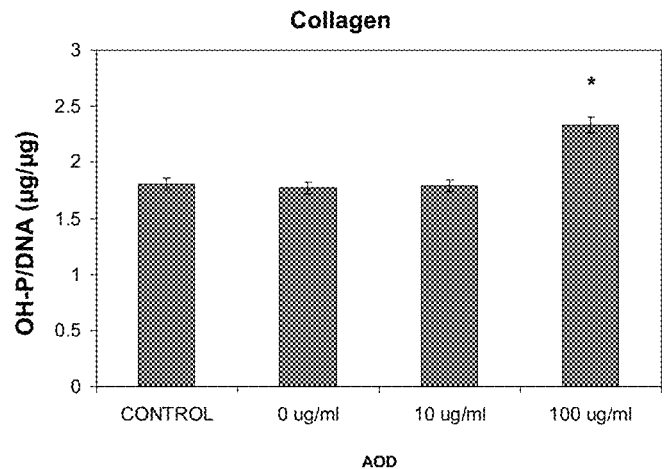
FIG. 3 shows collagen content for chondrocyte culture for 3 weeks on filter with treatment with AOD (SEQ ID NO:1).

AOD9604 (100 µg/ml) enhanced cartilage repair by increasing proteoglycan and collagen content of the tissue as determined at 3 weeks of culture (FIG. 2 and FIG. 3).

In the figures AOD9604 is referred to as AOD.

Example 2: Effect of AOD on Native Cartilage

Methods

Cartilage explants were taken from calf metacarpal-carpal joints and placed in culture in Ham's F-12 supplemented with 20% fetal bovine serum (FBS) in the presence and absence of AOD9604 (SEQ ID NO: 1) (10 or 100 µg/ml) for 1 week or (100 or 500 µg/ml) for 2 weeks.

Assessment of Tissue

The tissue was harvested and water content and dry weight measured. The tissue was then digested with papain (Sigma, 40 µg/ml) for 48 h at 65° C. DNA content was determined using the Hoechst 33258 dye binding assay (Polysciences) and fluorometry (excitation 365 nm, emission 458 nm). Proteoglycan content was determined by measuring the amount of sulphated glycosaminoglycans using the dimethylmethylene blue dye binding assay and spectrophotometry (525 nm). Collagen content was determined by measuring the hydroxyproline content of an aliquot of the papain digest hydrolyzed in 6N HCl for 18 h at 110° C. The hydroxyproline content was determined using the chloramine-T/Ehrlich's reagent assay and spectrophotometry (560 nm). The cellularity was quantified by measuring the DNA content using Hoescht 33258 dye binding assay (Polysciences) and fluorometry (excitation 365 nm, emission 458 nm).

Statistical Analysis

All experiments were done three times and each condition was done in triplicate. The data was expressed as mean±SD. The data was expressed as mean±SD. Significance was determined using two way ANOVA followed by Tukey's post hoc test when multiple groups were being evaluated. T test was utilized if 2 groups were being compared. Significance was assigned at p values <0.05.

Results

Figure 4:
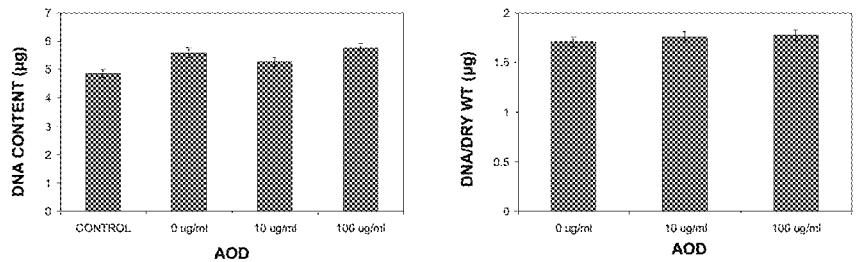
FIG. 4 shows that AOD (SEQ ID NO:1) has no effect on the DNA content of native cartilage.
Figure 5:
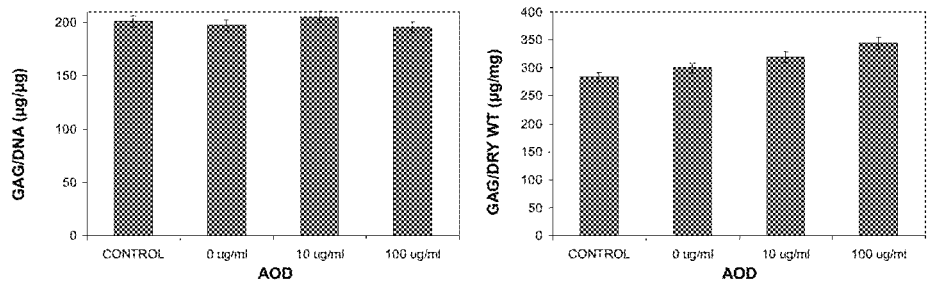
FIGS. 5 and 7 show that AOD (SEQ ID NO:1) does not affect proteoglycan content of native cartilage.
Figure 6:
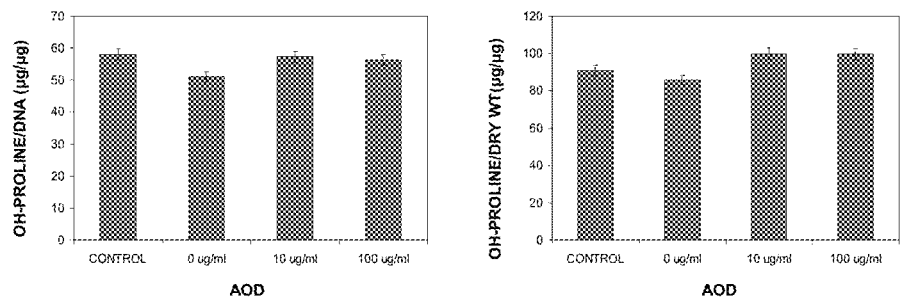
FIGS. 6 and 8 show that AOD (SEQ ID NO:1) does not affect collagen content of native cartilage.
Figure 7:
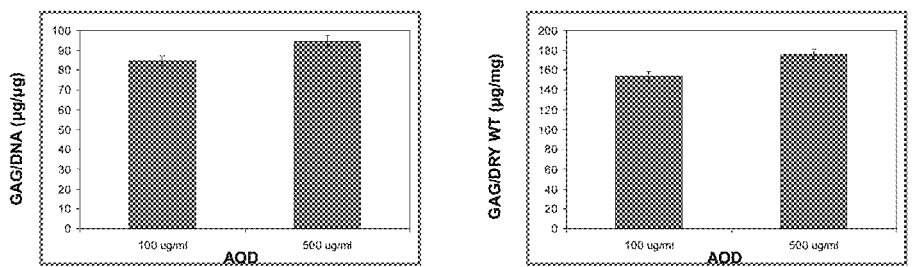
Figure 8:
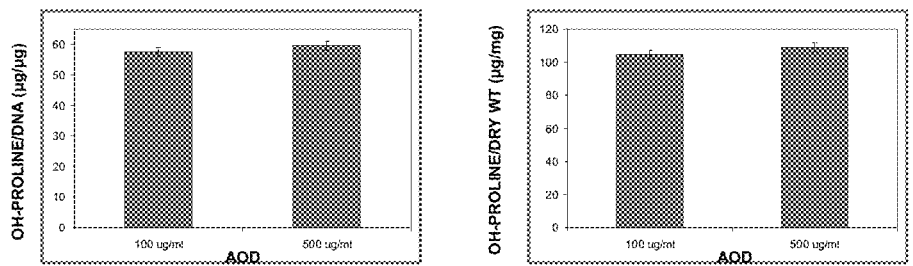

AOD was not toxic to cells at concentrations up to 500 µg/ml for 2 weeks of treatment as there was no significant change in DNA content in that time period (FIG. 4).

AOD9604 had no effect on native cartilage at concentrations of AOD of 500 µg/ml (FIGS. 5-8).

In the figures AOD9604 is referred to as AOD.

Conclusions

1) AOD9604 had a positive (anabolic) on cartilage tissue formation suggesting AOD would be appropriate to use to stimulate cartilage repair.

2) AOD9604 has no effect on intact cartilage.

Example 3: Effect of Peptide AOD9604 on Myoblast Differentiation into Muscle Cells In Vitro Methods
Cell Culture and Treatment C2C12 were grown in monolayer culture in DMEM (high glucose) supplemented with 10% fetal bovine serum under standard cell culture conditions. The cells were passaged at 60-70% confluence. The effect of AOD9604 (SEQ ID NO: 1) on cell proliferation was determined by growing the cells (3000 cells/cm$^2$) in the absence or presence of AOD9604 (10 and 100 µg/ml) for 3 days. The DNA content was then quantified. The cells were digested by papain and DNA content determined using the Hoechst 33258 dye binding assay (Polysciences) and fluorometry (excitation 365 nm, emission 458 nm).

Assessment of Cell Differentiation

C2C12 ($2\times10^3$ cells/cm$^2$) were grown in DMEM and 10% FBS. Differentiation was induced by replacing growth media with differentiation media which consists of DMEM supplemented with 2% horse serum. The cells were grown in the absence or presence of AOD9604 (10 or 100 µg/ml). The cells were fixed in 4% paraformaldehyde and co-stained for myogenin (a muscle specific muscle marker (transcription factor) 1/250 Tris-Triton X buffer) and Bodipy (cytoplasmic stain, Invitrogen, 1/1000 PBS). The number of cells stained for myogenin were counted in 4 random fields (up to 100 cells/field) (n=4). The percent of cells that stained positively for myogenin was calculated.

For myotube quantification the cells were stained with Bodipy (Invitrogen, 1/1000 PBS) according to the manufacturer's directions. The number of myotubes that developed over 72 hours was determined and expressed as a percent of total cells in culture (n=3, 100 cells/culture).

Statistical Analysis

The data was expressed as mean±SD. The data was expressed as mean±SD. Significance was determined using two way ANOVA followed by Tukey's post hoc test when multiple groups were being evaluated. T test was utilized if 2 groups were being compared. Significance was assigned at p values <0.05.

Results

Figure 9:
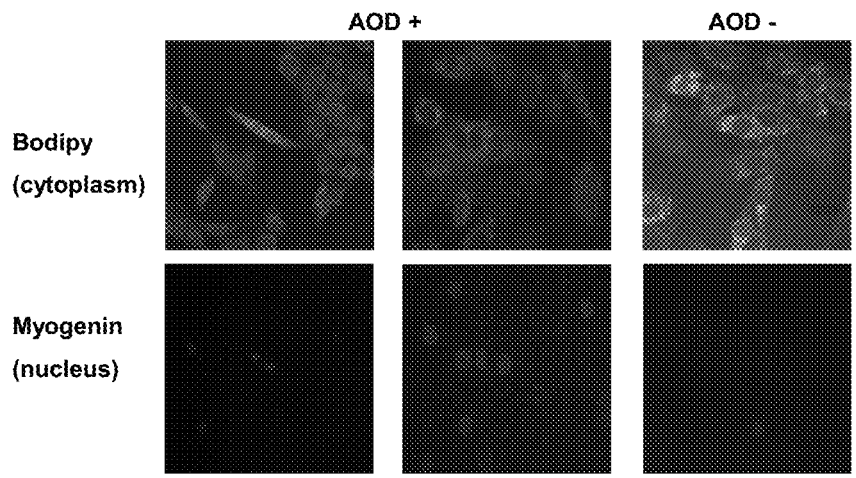
FIG. 9 shows that AOD (SEQ ID NO:1) induces differentiation of C2C12 cells into myoblasts after 24 hours of treatment.
Figure 10:
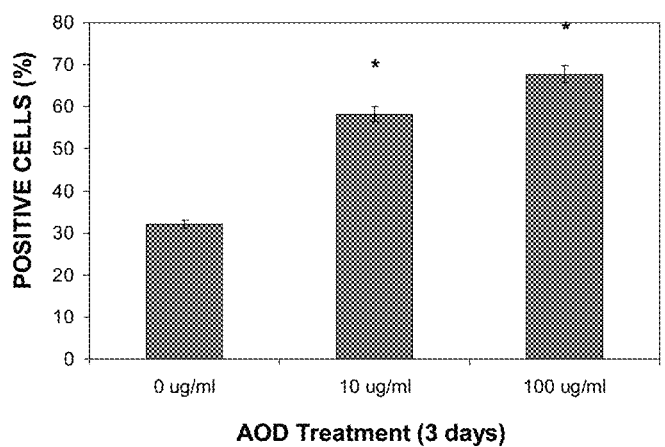
FIG. 10 shows that AOD (SEQ ID NO:1) induces differentiation of C2C12 cells into myoblasts after 3 days of treatment.
Figure 11:
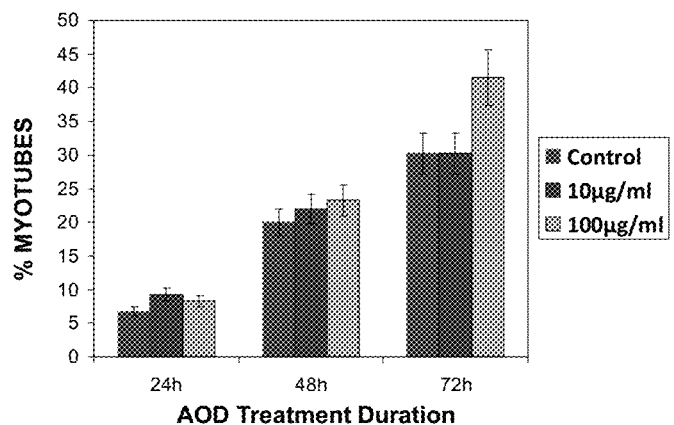
FIGS. 11 and 12 show that AOD (SEQ ID NO:1) treatment does not enhance myotube Formation or alter cell proliferation.
Figure 12:
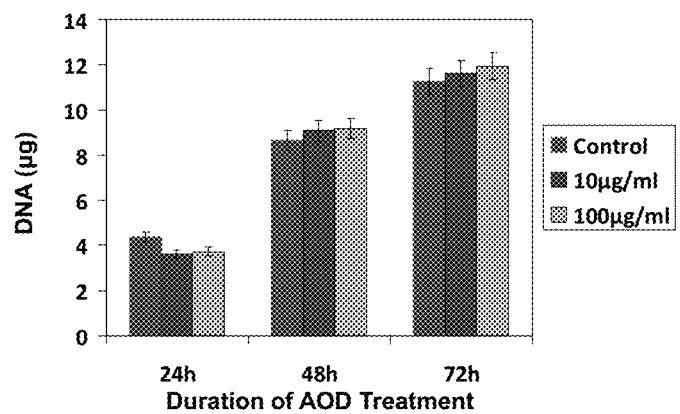

AOD9604 enhances C2C12 differentiation into myoblasts by 72 hours at doses as low as 10 µg/ml (FIGS. 9 and 10). AOD9604 had no affect on the formation of myotubes (FIG. 11). AOD9604 did not affect cell proliferation (FIG. 12). In the figures AOD9604 is referred to as AOD.

Conclusion

AOD9604 enhances differentiation to myoblasts and may be appropriate to use to enhance muscle formation.

Example 4: Effect of Intra-Articular Administration of AOD9604 in a Rabbit Collagenase Model of Osteoarthritis Given Alone and in Combination with HA Study Design The study followed the protocols as described in Kim et al., (2010) J Korean Med Sci 25:776-780, which demonstrated the therapeutic effect of intra-articular administration of hyaluronic acid (HA) with and without AOD9604 (SEQ ID NO:1). AOD9604 (SEQ ID NO: 1) was provided by Metabolic Pharmaceutical Pty Ltd.

Species: New Zealand White Rabbit
Sex: Male
Age: 12 weeks
Number of Rabbits: 32

Treatments groups: 32 rabbits were each given a 2 mg collagenase injection into their right knee joint, followed by a second injection 3 days later to induce osteoarthritis. After 4 weeks, the rabbits were divided into 4 groups of 8 for subsequent treatments.

Group 1 received 4 weekly injections of vehicle (disease control group).

Group 2 received 4 weekly injections of 6 mg of HA-hyuran-plus (HA positive control group).

Group 3 received 4 weekly injections of 0.25 mg of AOD9604 (AOD only group).

Group 4 received 4 weekly injections of both HA and AOD9604 (combination group).

Clinical observations were made by direct observation daily to assess lameness (as described in Kim et al., (2010) supra). At 9 weeks post initial collagenase injection the animals were euthanized.

Gross observation of the right and left knee joints was performed after dissection and scored for damage (as described in Kim et al., (2010) supra). Histological analysis of lateral and medial condyles from each joint was performed and scored.

Figure 13:
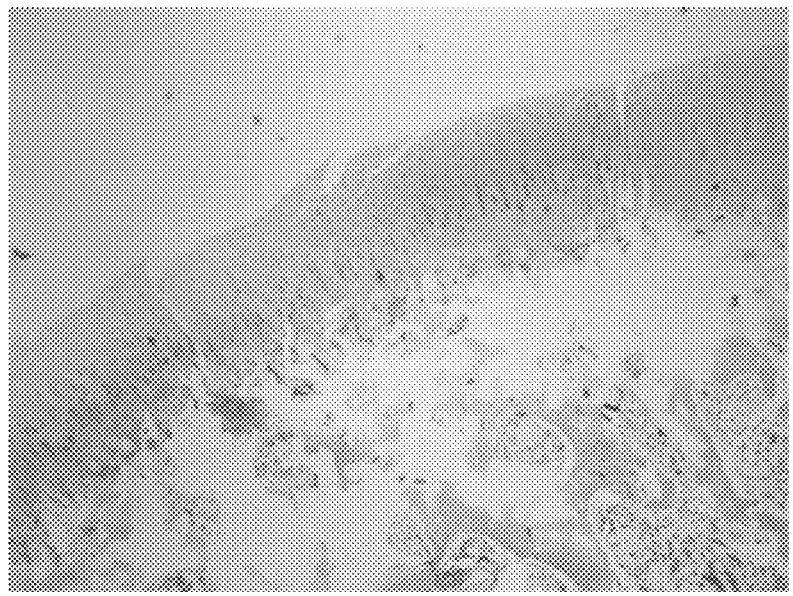
FIG. 13 shows histological analysis of lateral and medial condyles of the right knee joint of a rabbit osteoarthritis model treated with Group 1 (4 weekly injections of vehicle).
Figure 14:
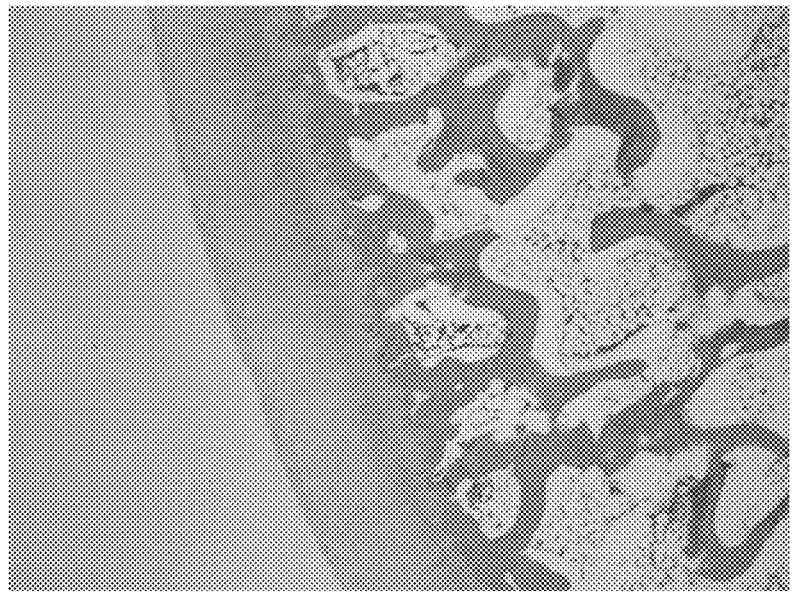
FIG. 14 shows histological analysis of lateral and medial condyles of the right knee joint of a rabbit osteoarthritis model treated with Group 2 (4 weekly injections of 6 mg of HA-hyuran-plus).
Figure 15:
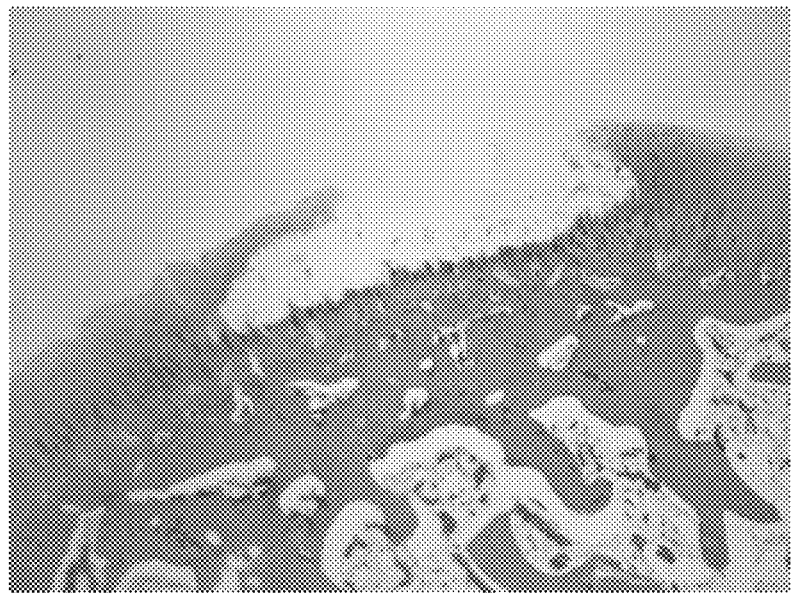
FIG. 15 shows histological analysis of lateral and medial condyles of the right knee joint of a rabbit osteoarthritis model treated with Group 3 (4 weekly injections of 0.25 mg of AOD9604).
Figure 16:
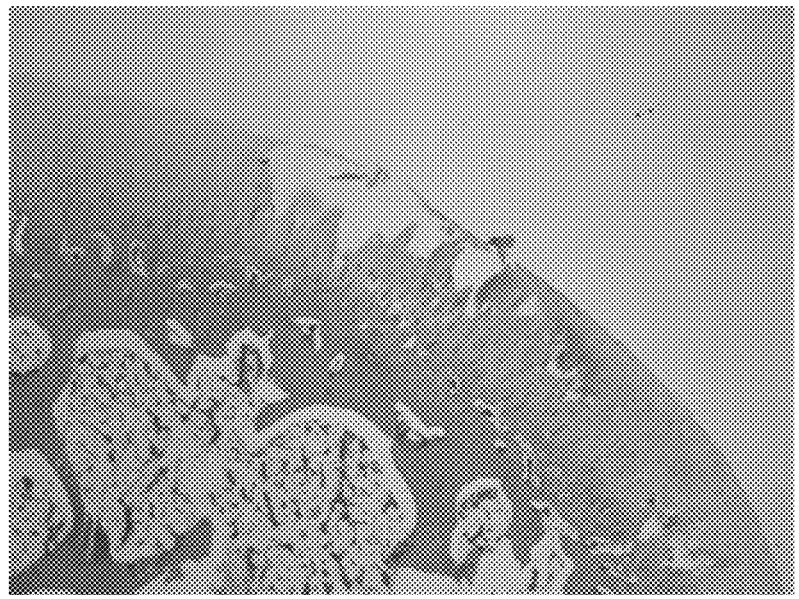
FIG. 16 shows histological analysis of lateral and medial condyles of the right knee joint of a rabbit osteoarthritis model treated with Group 4 (4 weekly injections of both HA and AOD9604).

A statistical analysis of the data was performed and the results are shown in FIGS. 13 (Group 1), 14 (Group 2), 15 (Group 3) and 16 (Group 4). The results indicate that AOD9604 (SEQ ID NO:1) has regenerative power compared to control and that HA and AOD9694 (SEQ ID NO: 1) provide a similar amount of improvement at this point in time.

Example 5: Case Study—Infection

The subject was a 46 year old male. Nail puncture in the left foot. The subject described a very swollen foot with a high degree of redness for two centimeter circumference around the punctured site. There was also a high degree of tenderness. The swelling was identified throughout the right side of the left foot and through the fourth and fifth phalanges. Some swelling was noted back into the ankle joint. Symptoms consistent with *Clostridium tetani* infection.

Dosage:

Three 360 mcg doses of AOD9604 (SEQ ID NO:1) subcutaneously around the infected area per day. Each individual dose represented an intake of 0.3 ml at 1200 mcg per ml per dose. 4 days.

Main Observations:

By day five the subject was very happy with both the pain and functionality in the region. He was able to fully cloth the foot with a shoe and could resume general weight bearing activity. The subject resumed full running and moderate weight lifting activity on day eight. The subject also noted that the pain was considerably reduced by around three of the injections. The majority of this pain reduction was associated with the swelling from the infection. The tissue discomfort due to disruption resolved at around day five. The subject felt all symptoms and any other associated minor discomfort had fully resolved at around day eight. No other chemotherapeutic intervention or antimicrobiotics used in the treatment.

Example 6: Case Study—Calf Muscle

The subject was a 24 year old male professional footballer. The athlete incurred at 1.5 cm tear on his soleus near the adjacent aponeurosis to the gastrocnemius. The MRI displayed some associated bleeding and contusion. A 1.5 cm tear is considered a moderately large tear for the region. The MRI indicated that a mass of blood and edema had positioned itself near the anterior aponeurosis insertion onto the median septum. The fibre tears were directional with the orientation of the fibres. The length of the tear was 1.5 cm.

Dosage:

The subject undertook an intervention of AOD9604 (SEQ ID NO: 1) at 600 mcg per dose. He applied one ml twice daily. The transdermal application was at 600 mcg per ml. The total application was 20 ml.

Main Observations:

The athlete's injury was resolved in two weeks. This was considerably a reduction in time frame given the original nature of the injury. The MRI confirmed that that full integrity had returned to the injury. No bleeding or edema was identified on the follow up MRI. Also at this point the athlete had returned to full weight bearing activities. The athlete indicated that there was no residual pain or discomfort associated with the original injury. There was no awareness of the area with the return to exercise. There was no immediate pain or discomfort once the weight bearing capacity was fully resumed. The athlete also noted that the pain associated with the injury had started to diminish quite rapidly after the injury application of the transdermal. He indicated that there was no resumption of any pathology and in relation to pain or inflammation on return. He was comfortable with running mechanics and he commented that no discomfort was noted. The athlete considered that the injury had returned to full function.

Example 7: Case Study—Hamstring Muscle

The subject was a 22 year old male professional footballer. The athlete incurred at 2.0 cm tear to the long head of his bicep femoris. The MRI indicated that a mass of blood and edema was prominant near the upper third of the long head muscle belly. Some fibre disruption was noted below the tendon junction coming from the insertion. The length of the tear was 1.5 cm. The fusiform belly region around the injury was highly inflamed.
Dosage:
The subject undertook an intervention of AOD9604 (SEQ ID NO: 1) at 600 mcg per dose. He applied one ml twice daily. The transdermal application was at 600 mcg per ml. The total application was 40 ml.
Main Observations.
The athlete's injury was resolved in three weeks. It was considered that was a significant reduction in the time frame expected given the original pathology of the injury. The MRI confirmed that that full integrity had returned to the bicep femoris long head. No residual bleeding or edema was identified on the follow up MRI. The athlete had returned to full weight bearing activities at the conclusion of the three week application of the transdermal. This was thought to be ahead of schedule. The athlete noted that there was no residual pain or discomfort associated with the original injury once returning to full weight bearing duties. There was no awareness of the area with the return. There was no immediate pain or discomfort identified with the full weight bearing capacity. The athlete felt that the pain associated with the injury had started to diminish within the first week of application of the transdermal. He indicated that there was no aggravation of pathology and no pain or inflammation. He had full comfort with the running mechanics and no discomfort was noted during or after exercise. Within the first week of the return to full weight bearing activities the athlete experienced no limitations to weight bearing capacity and was considered to have a full return to function.

Example 8—Case Study—Shoulder Tendon

The subject was a 23 year old male professional footballer. The athlete incurred some fibre disruption at the junction of supraspinatus tendon insertion. The MRI indicated an area of 1.0 cm within the disruptive pathology. The MRI indicated that the disruption approached most superior facet of the greater tubercle of the humerus. Most of the affected area was the muscular portion of the junction. The MRI indicated an area of 1.0 cm within the disruptive pathology. The athlete indicated that the pain associated with the area was noticeable for around 5 weeks indicating some chronicity to the injury. The athlete had been restricted in both the range of motion he could employ for the injured site as well as the amount of weight bearing activity he could engage for the area. He had been finding it difficult to abduct the arm at the shoulder joint. He found difficulty in resisting inferior gravitational forces placed across the shoulder joint and found aggravation with any downward pull with weight of the upper limb.
Dosage:
The subject undertook an intervention of AOD9604 (SEQ ID NO: 1) at 600 mcg per dose. He applied one ml twice daily. The transdermal application was at 600 mcg per ml. The total application was 30 ml.
Main Observations:
The athlete's injury was resolved in three weeks. Subsequent MRI confirmed that that full integrity had returned to the junctional area. The athlete also had returned to full weight bearing activities and rotation activity with the area. The athlete felt that there was no residual pain or discomfort associated with either movement or resistant work with the region. There was no awareness of the area with the return to exercise in either the rotation or weight bearing components. The athlete confirmed that there was no immediate pain or discomfort once the weight bearing capacity was fully resumed and no pain, inflammation or awareness of the injury could be identified post training. There was no re-aggravation of the injury at any stage. The athlete also noted that the pain associated with the injury had started to diminish by the end of the first week of the application of the transdermal.

Example 9—Case Study—Corked Quad—Hematoma

The subject was a 24 year old male professional footballer. The athlete incurred a contusion to the rectus femoris adjacent to the central tendon. The MRI indicated an area of 2.0 cm area for the contusion. The MRI indicated that there was fibre disruption within the middle of the rectus femoris just adjacent to the region of the central tendon. The MRI indicated that the area of disruption was 2.0 cm. There was a minor degree of associated edema associated with the pathology. The MRI confirmed that there was fibre disruption but no true tear. The central tendon remained intact. The injury was an acute injury. The athlete identified discomfort on weight bearing movement and the mass was easily palpatable. Any hip flexion movement could induce discomfort and awareness of the injury. Although the muscle is not considered a dominant muscle in knee extension movement the affected area was painful and inducing discomfort with such work.
Dosage:
The subject undertook an intervention of AOD9604 (SEQ ID NO: 1) at 600 mcg per dose. He applied one ml twice daily. The transdermal application was at 600 mcg per ml. The total application was 20 ml.
Main Observations:
The athlete's injury was resolved in two weeks. The area for the contusion was noted to be clear of any bleeding or edema on subsequent MRI. The MRI confirmed a return to full anatomical integrity for the injured area. The athlete returned to full weight bearing activity experiencing no issues with mechanical load or running mechanics. There were no issues with resumption of contact. The athlete confirmed that there was no immediate pain or discomfort once the weight bearing capacity was fully resumed, The athlete felt that no pain, inflammation or awareness of the injury could be identified post training. There was no re-aggravation of the injury at any stage either through running, weight bearing or contact. The athlete noted that the pain associated with the injury had started to diminish by the end of the first week of the application of the transdermal though some mass could still palpated in the injured area.

---

The invention claimed is:

1. A method for improving muscle, ligament or tendon mass, repair, form or strength in a subject, the method comprising administering to a subject in need of such treatment an effective amount of a peptide that is up to 50 amino acid residues in length and comprises amino acid residues 182-189 of human growth hormone or the corresponding region from any one of SEQ ID Nos: 1-41, which peptide does not include the domain of growth hormone responsible for IGF-1 production.

2. The method of claim 1, wherein the peptide comprises a carboxyl-terminal sequence from human growth hormone or a carboxyl terminal sequence from a growth hormone of a non-human animal.

3. The method of claim 1, wherein the peptide is administered in combination with mesenchymal stem cell therapy.

4. The method of claim 1, wherein the peptide is administered to a subject treated with stem cell therapy for joint and muscle repair.

5. The method of claim 1, wherein the peptide comprises amino acids 182-189 of human growth hormone.

6. The method of claim 1, wherein the peptide comprises amino acids 177-191 of human growth hormone.

7. The method of claim 1, wherein the peptide comprises a sequence selected from SEQ ID NO: 1-5, 22-24, 27-34 39 and 41.

8. The method of claim 1, wherein the peptide consists of a sequence selected from SEQ ID NO: 1-5, 22-24, 27-34 39 and 41.

9. The method of claim 1, wherein the peptide is administered by intra-articular administration with hyaluronic acid.

* * * * *

```
                              SEQUENCE LISTING

<160> NUMBER OF SEQ ID NOS: 41

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr Leu Arg Ile Val Gln Cys Arg Ser Val Glu Gly Ser Cys Gly Phe
1               5                   10                  15

<210> SEQ ID NO 2
<211> LENGTH: 26
<212> TYPE: PRT
<213> ORGANISM: Homo sapiens

<400> SEQUENCE: 2

Phe Arg Lys Asp Met Asp Lys Val Glu Thr Phe Leu Arg Ile Val Gln
1               5                   10                  15

Cys Arg Ser Val Glu Gly Ser Cys Gly Phe
            20                  25

<210> SEQ ID NO 3
<211> LENGTH: 26
<212> TYPE: PRT
<213> ORGANISM: Homo sapiens

<400> SEQUENCE: 3

Phe Arg Lys Asp Met Asp Lys Val Glu Thr Phe Leu Arg Ile Val Gln
1               5                   10                  15

Cys Arg Ser Val Glu Gly Ser Cys Gly Phe
            20                  25

<210> SEQ ID NO 4
<211> LENGTH: 26
<212> TYPE: PRT
<213> ORGANISM: Homo sapiens

<400> SEQUENCE: 4

Phe Arg Lys Asp Met Asp Lys Val Glu Thr Phe Leu Arg Met Val Gln
1               5                   10                  15

Cys Arg Ser Val Glu Gly Ser Cys Gly Phe
            20                  25

<210> SEQ ID NO 5
<211> LENGTH: 26
<212> TYPE: PRT
<213> ORGANISM: Macaca mulatta

<400> SEQUENCE: 5

Phe Arg Lys Asp Met Asp Lys Ile Glu Thr Phe Leu Arg Ile Val Gln
1               5                   10                  15

Cys Arg Ser Val Glu Gly Ser Cys Gly Phe
            20                  25

<210> SEQ ID NO 6
```

```
<211> LENGTH: 27
<212> TYPE: PRT
<213> ORGANISM: Rattus sp.

<400> SEQUENCE: 6

Phe Lys Lys Asp Leu His Lys Ala Glu Thr Tyr Leu Arg Val Met Lys
1               5                   10                  15

Cys Arg Arg Phe Ala Glu Ser Ser Cys Ala Phe
            20                  25

<210> SEQ ID NO 7
<211> LENGTH: 27
<212> TYPE: PRT
<213> ORGANISM: Mus sp.

<400> SEQUENCE: 7

Phe Lys Lys Asp Leu His Lys Ala Glu Thr Tyr Leu Arg Val Met Lys
1               5                   10                  15

Cys Arg Arg Phe Ala Glu Ser Ser Cys Ala Phe
            20                  25

<210> SEQ ID NO 8
<211> LENGTH: 27
<212> TYPE: PRT
<213> ORGANISM: Unknown
<220> FEATURE:
<223> OTHER INFORMATION: Description of Unknown: Hamster growth hormone
      peptide

<400> SEQUENCE: 8

Phe Lys Lys Asp Leu His Lys Ala Glu Thr Tyr Leu Arg Val Met Lys
1               5                   10                  15

Cys Arg Arg Phe Ala Glu Ser Ser Cys Ala Phe
            20                  25

<210> SEQ ID NO 9
<211> LENGTH: 27
<212> TYPE: PRT
<213> ORGANISM: Balaenoptera physalus

<400> SEQUENCE: 9

Phe Lys Lys Asp Leu His Lys Ala Glu Thr Tyr Leu Arg Val Met Lys
1               5                   10                  15

Cys Arg Arg Phe Val Glu Ser Ser Cys Ala Phe
            20                  25

<210> SEQ ID NO 10
<211> LENGTH: 27
<212> TYPE: PRT
<213> ORGANISM: Balaenoptera borealis

<400> SEQUENCE: 10

Phe Lys Lys Asp Leu His Lys Ala Glu Thr Tyr Leu Arg Val Met Lys
1               5                   10                  15

Cys Arg Arg Phe Val Glu Ser Ser Cys Ala Phe
            20                  25

<210> SEQ ID NO 11
<211> LENGTH: 27
<212> TYPE: PRT
<213> ORGANISM: Unknown
<220> FEATURE:
<223> OTHER INFORMATION: Description of Unknown: Fox, dog and cat growth
      hormone peptide
```

```
<400> SEQUENCE: 11

Phe Lys Lys Asp Leu His Lys Ala Glu Thr Tyr Leu Arg Val Met Lys
1               5                   10                  15

Cys Arg Arg Phe Val Glu Ser Ser Cys Ala Phe
            20                  25

<210> SEQ ID NO 12
<211> LENGTH: 27
<212> TYPE: PRT
<213> ORGANISM: Unknown
<220> FEATURE:
<223> OTHER INFORMATION: Description of Unknown: Mink growth hormone
      peptide

<400> SEQUENCE: 12

Phe Lys Lys Asp Leu His Lys Ala Glu Thr Tyr Leu Arg Val Met Lys
1               5                   10                  15

Cys Arg Arg Phe Val Glu Ser Ser Cys Ala Phe
            20                  25

<210> SEQ ID NO 13
<211> LENGTH: 27
<212> TYPE: PRT
<213> ORGANISM: Unknown
<220> FEATURE:
<223> OTHER INFORMATION: Description of Unknown: Cattle growth hormone
      peptide

<400> SEQUENCE: 13

Phe Arg Lys Asp Leu His Lys Thr Glu Thr Tyr Leu Arg Val Met Lys
1               5                   10                  15

Cys Arg Arg Phe Gly Glu Ala Ser Cys Ala Phe
            20                  25

<210> SEQ ID NO 14
<211> LENGTH: 27
<212> TYPE: PRT
<213> ORGANISM: Ovis aries

<400> SEQUENCE: 14

Phe Arg Lys Asp Leu His Lys Thr Glu Thr Tyr Leu Arg Val Met Lys
1               5                   10                  15

Cys Arg Arg Phe Gly Glu Ala Ser Cys Ala Phe
            20                  25

<210> SEQ ID NO 15
<211> LENGTH: 27
<212> TYPE: PRT
<213> ORGANISM: Capra hircus

<400> SEQUENCE: 15

Phe Arg Lys Asp Leu His Lys Thr Glu Thr Tyr Leu Arg Val Met Lys
1               5                   10                  15

Cys Arg Arg Phe Gly Glu Ala Ser Cys Ala Phe
            20                  25

<210> SEQ ID NO 16
<211> LENGTH: 27
<212> TYPE: PRT
<213> ORGANISM: Sus sp.

<400> SEQUENCE: 16
```

```
Phe Lys Lys Asp Leu His Lys Ala Glu Thr Tyr Leu Arg Val Met Lys
1               5                   10                  15

Cys Arg Arg Phe Val Glu Ser Ser Cys Ala Phe
            20                  25

<210> SEQ ID NO 17
<211> LENGTH: 27
<212> TYPE: PRT
<213> ORGANISM: Vicugna pacos

<400> SEQUENCE: 17

Phe Lys Lys Asp Leu His Lys Ala Glu Thr Tyr Leu Arg Val Met Lys
1               5                   10                  15

Cys Arg Arg Phe Val Glu Ser Ser Cys Ala Phe
            20                  25

<210> SEQ ID NO 18
<211> LENGTH: 27
<212> TYPE: PRT
<213> ORGANISM: Equus sp.

<400> SEQUENCE: 18

Phe Lys Lys Asp Leu His Lys Ala Glu Thr Tyr Leu Arg Val Met Lys
1               5                   10                  15

Cys Arg Arg Phe Val Glu Ser Ser Cys Ala Phe
            20                  25

<210> SEQ ID NO 19
<211> LENGTH: 27
<212> TYPE: PRT
<213> ORGANISM: Unknown
<220> FEATURE:
<223> OTHER INFORMATION: Description of Unknown: Elephant growth hormone
      peptide

<400> SEQUENCE: 19

Phe Lys Lys Asp Leu His Lys Ala Glu Thr Tyr Leu Arg Val Met Lys
1               5                   10                  15

Cys Arg Arg Phe Val Glu Ser Ser Cys Ala Phe
            20                  25

<210> SEQ ID NO 20
<211> LENGTH: 27
<212> TYPE: PRT
<213> ORGANISM: Unknown
<220> FEATURE:
<223> OTHER INFORMATION: Description of Unknown: Ancestral mammal growth
      hormone peptide

<400> SEQUENCE: 20

Phe Lys Lys Asp Leu His Lys Ala Glu Thr Tyr Leu Arg Val Met Lys
1               5                   10                  15

Cys Arg Arg Phe Val Glu Ser Ser Cys Ala Phe
            20                  25

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
```

<223> OTHER INFORMATION: Pen
<220> FEATURE:
<221> NAME/KEY: MOD_RES
<222> LOCATION: (13)..(13)
<223> OTHER INFORMATION: Pen

<400> SEQUENCE: 21

Leu Arg Ile Val Gln Xaa Arg Ser Val Glu Gly Ser Xaa Gly Phe
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term CH3CO

<400> SEQUENCE: 22

Leu Arg Ile Val Gln Cys Arg Ser Val Glu Gly Ser Cys Gly Phe
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H

<400> SEQUENCE: 23

Leu Arg Ile Val Gln Cys Arg Ser Val Glu Gly Ser Cys Gly Phe
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term CONH2

<400> SEQUENCE: 24

Leu Arg Ile Val Gln Cys Arg Ser Val Glu Gly Ser Cys Gly Phe
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Arg Ile Val Gln Cys Lys Ser Val Glu Gly Ser Cys Gly Phe
1               5                   10                  15

<210> SEQ ID NO 26
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MISC_FEATURE
<222> LOCATION: (7)..(10)
<223> OTHER INFORMATION: Amide bond between positions

<400> SEQUENCE: 26

Leu Arg Ile Val Gln Cys Lys Ser Val Glu Gly Ser Cys Gly Phe
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Leu Arg Ile Val Gln Cys Arg Ser Val Glu Gly Ser Cys Gly Phe
1               5                   10                  15

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Lys Leu Arg Ile Val Gln Cys Arg Ser Val Glu Gly Ser Cys Gly
1               5                   10                  15

Phe

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Arg Ile Val Gln Cys Arg Ser Val Glu Gly Ser Cys Gly Phe
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu Lys Ile Val Gln Cys Arg Ser Val Glu Gly Ser Cys Gly Phe
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 31

Leu Arg Ala Val Gln Cys Arg Ser Val Glu Gly Ser Cys Gly Phe
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Arg Lys Val Gln Cys Arg Ser Val Glu Gly Ser Cys Gly Phe
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Arg Ile Ala Gln Cys Arg Ser Val Glu Gly Ser Cys Gly Phe
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Leu Arg Ile Val Ala Cys Arg Ser Val Glu Gly Ser Cys Gly Phe
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Arg Ile Val Gln Cys Arg Ala Val Glu Gly Ser Cys Gly Phe
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Arg Ile Val Gln Cys Arg Ser Ala Glu Gly Ser Cys Gly Phe
1               5                   10                  15

<210> SEQ ID NO 37
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 37

Leu Arg Ile Val Gln Cys Arg Ser Val Glu Ala Ser Cys Gly Phe
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Arg Ile Val Gln Cys Arg Ser Val Glu Gly Ala Cys Gly Phe
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Arg Ile Val Gln Cys Arg Ser Val Glu Gly Ser Cys Ala Phe
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: D-Ala
<220> FEATURE:
<221> NAME/KEY: MOD_RES
<222> LOCATION: (14)..(14)
<223> OTHER INFORMATION: D-Ala

<400> SEQUENCE: 40

Leu Arg Ile Val Gln Cys Arg Ser Val Glu Ala Ser Cys Ala Phe
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Arg Ile Val Gln Cys Arg Ser Val Glu Gly Ser Cys Gly Ala
1               5                   10                  15
```